(12) United States Patent
Sörös et al.

(10) Patent No.: US 8,309,712 B2
(45) Date of Patent: Nov. 13, 2012

(54) INDUSTRIAL PROCESS FOR THE PREPARATION OF 17- HYDROXY-6BETA,7BETA;15BETA, 16BETA-BISMETHYLENE-3-OXO-17ALPHA-PREGN-4-ENE-21-CARBOXYLIC ACID γ-LACTONE AND KEY INTERMEDIATES FOR THIS PROCESS

(75) Inventors: Béla Sörös, Budapest (HU); Judit Horváth, Budapest (HU); György Gálik, Albertirsa (HU); József Bódi, Budapest (HU); Zoltán Tuba, Budapest (HU); Sándor Mahó, Budapest (HU); Gábor Balogh, Budapest (HU); Antal Aranyi, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 1230 days.

(21) Appl. No.: 11/719,333

(22) PCT Filed: Oct. 11, 2005

(86) PCT No.: PCT/HU2005/000110
§ 371 (c)(1),
(2), (4) Date: May 15, 2007

(87) PCT Pub. No.: WO2006/059167
PCT Pub. Date: Jun. 8, 2006

(65) Prior Publication Data
US 2008/0200668 A1 Aug. 21, 2008

(30) Foreign Application Priority Data
Nov. 30, 2004 (HU) .................................... 0402465

(51) Int. Cl.
*C07J 53/00* (2006.01)
(52) U.S. Cl. ........................................................ 540/15
(58) Field of Classification Search .................... 540/15
See application file for complete search history.

(56) References Cited

U.S. PATENT DOCUMENTS

| | | |
|---|---|---|
| 3,470,160 A | 9/1969 | Schmidt et al. |
| 3,676,467 A | 7/1972 | Furst et al. |
| 4,129,564 A | 12/1978 | Wiechert et al. |
| 4,435,327 A | 3/1984 | Petzoldt et al. |
| 4,614,616 A | 9/1986 | Petzoldt et al. |
| 6,121,465 A | 9/2000 | Mohr et al. |

FOREIGN PATENT DOCUMENTS

DE 27 46 298 A1 4/1979

OTHER PUBLICATIONS

Norman et al., Contraceptive Hormone REplacement Therapy Aldosterone Antagonist Progestogen, Drugs of the Future, Dec. 2000, pp. 1247-1256, vol. 25 No. 12.*
K. Petzoldt et al., A Novel Synthetic Route to the Aldosterone-Antagonist Spirorenone, Angewandte Chemie International Edition, 1983, pp. 406-407, vol. 22, No. 5.
D. Bittler et al., Synthesis of Spirorenone—A Novel Highly Active AldoSterone Antagonist, Angewandte Chemie International Edition, 1982, pp. 696-697, vol. 21, No. 9.
A.V. Kamernitskii et al., Transformed Steroids . . . , Bulletin of the Academy of Sciences of the USSR, 1985, pp. 1743-1748, vol. 34.

* cited by examiner

*Primary Examiner* — Barbara P Badio
(74) *Attorney, Agent, or Firm* — Jason D. Voight

(57) ABSTRACT

The invention relates to an industrial process for the preparation of 17-hydroxy-6β,7β;15β,16β-bismethylene-3-oxo-17α-pregn-4-ene-21-carboxylic acid γ-lactone of formula (I), and to the key-intermediates for this process.

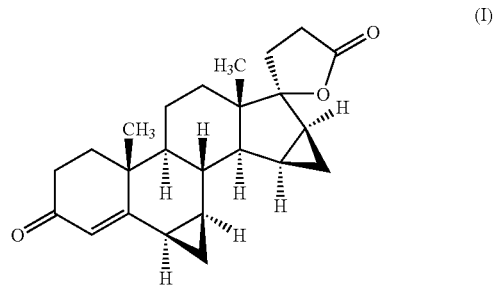

(I)

14 Claims, No Drawings

INDUSTRIAL PROCESS FOR THE PREPARATION OF 17- HYDROXY-6BETA,7BETA;15BETA, 16BETA-BISMETHYLENE-3-OXO-17ALPHA-PREGN-4-ENE-21-CARBOXYLIC ACID Y-LACTONE AND KEY INTERMEDIATES FOR THIS PROCESS

This is the National Stage of International Application PCT/HU2005/000110, filed Oct. 11, 2005.

The object of the invention is an industrial process for the preparation of the known 17-hydroxy-6β,7β;15β,16β-bismethylene-3-oxo-17α-pregn-4-ene-21-carboxylic acid γ-lactone (hereinafter: drospirenone) of the formula (I), as well as key intermediates for the synthesis.

The compound of the formula (I) is known by the name drospirenone in the therapy and is a synthetic progestin having also anti-mineralocorticoid and antiandrogenic effects. In combination with ethynylestradiol it is marketed under the name of Yasmin as an oral contraceptive.

For the preparation of drospirenone several processes are known in the chemical literature which differs in the starting material used and in the order of the reaction steps. Introduction of the functional groups is accomplished by known chemical methods. All processes are suitable for laboratory-scale use and a scale-up for industrial application may imply several unexpected problems.

A synthesis of drospirenone is first disclosed in the German patent specification DE 2,652,761. The synthesis starts from 3β-hydroxy-15β,16β-methyleneandrost-5-en-17-one which is reacted with 1-bromo-3,3-dimethoxypropane in tetrahydrofuran in the presence of lithium, followed by a cyclization in position 17 carried out in 70% acetic acid to give the "lactol-ether". The hydroxy and ether groups being present in the molecule were oxidized with cyclohexanone in the presence of aluminum isopropylate, then the double bond was izomerized by using 2N sulfuric acid to yield 17-hydroxy-15β,16β-methylene-3-oxo-17α-pregn-4-ene-21 carboxylic acid γ-lactone.

The "lactone" derivative was reacted with chloranil (2,3,5, 6-tetrachloro-2,5-cyclohexadiene-1,4-dione) in tert-butanol to form the "3-oxo-androsta-4,6-diene" in which a methylene group was introduced in positions 6,7 (by using trimethylsulfoxonium iodide and sodium hydride producing in situ a "methylide") giving the drospirenone.

For the preparation of 3β-hydroxy-15β,16β-methyleneandrost-5-ene-17-one (the starting material for the above synthesis) a five step reaction route is disclosed in the German patent specification DE 1,593,500.

The first drospirenone synthesis includes several reactions which cannot be realized at industrial scale and gave typically low yields. Purification of the intermediates and the end-product accomplished by chromatography gave also low yields (49%, 26% and 16%, respectively.

In the German patent specification DE 2,746,298 intermediates which can be used also for the preparation of drospirenon are described. To form double bonds (which are required for the introduction of the methylene groups), first hydroxyl groups were brought into the molecule via a microbiological process. The dehydroepiandrosterone—the starting material for the synthesis—was hydroxylated microbiologically to give 3β,7α,15α-trihydroxyandrost-5-ene-17-one which, in turn, was oxidized in an additional fermentation step to yield 7α,15α-dihydroxyandrost-4-ene-3,17-dione. Elimination of the hydroxy group in position 15 was accomplished with p-toluenesulfonic acid catalyst yielding the "4,6, 15-triene".

When the 7α,15α-dihydroxy derivative was acetylated with acetic anhydride in pyridine the 3-acetoxy-7α-hydroxy-androst-5,15-diene-17-one in one step was obtained, to said compound a methylene moiety was introduced in positions 15,16 by a process discussed above, the compound obtained was oxidized microbiologically and after elimination of water 15β,16β-methylenandrosta-4,6-diene-3,17-dione was obtained. Then the compound having the "diene" structure in the AB rings of the steroid was treated with ethylene glycol in the presence of orthoformic acid trialkyl ester and p-toluenesulfonic acid catalyst to give the ketal in a manner known per se, said ketal was reacted with dimethoxybromopropane in the presence of lithium as described above to yield the "17-acetal", which then was cyclized to form the corresponding "lactol-methyl ether" and this was subjected to Jones oxidation to give the corresponding "lactone". The intermediate obtained in such a way has a double bond in position 6,7 to which a methylene group can be introduced in a known manner.

Theoretically another synthesis route is described for the preparation of drospirenone in the European patent specification EP 051,143 and its equivalents (U.S. Pat. Nos. 4,416, 985 and 4,614,616). The process is also published in Angew. Chem. 94, 718-719 (1982). What is novel is that the 6β,7β-methylene group is formed in a stereospecific manner by the Simmons-Smith reaction.

The starting material of the process is 3β-hydroxy-15β, 16β-methyleneandrost-5-en-17-one. The hydroxy in 7β position is introduced in a fermentation process using Botryodiplodia malorum, the resultant compound is acetylated in a regioselective manner with pivalic anhydride in the presence of 4-dimethylaminopyridine yielding the corresponding 3β-pivaloyloxy derivative. Said pivaloyloxy derivative was reacted with tert-butyl hydroperoxide in the presence of VO (acetonylacetonate)$_2$ catalyst to give the 5β,6β-epoxy derivative which, in turn, was reacted with triphenylphosphine and carbon tetrachloride in dichloromethane to yield the 7α-chloro derivative. Said 7α-chloro derivative was reacted with zinc in a mixture of acetic acid and tetrahydrofuran yielding the 5β-hydroxy-15β,16β-methylene-3β-pivaloyloxyandrost-6-en-17-one which then was hydrolyzed with potassium hydroxide to give 3β,5β-dihydroxy-15β,16β-methyleneandrost-6-en-17-one.

Into the compound having a double bond in position 6 the methylene group was introduced by using diiodomethane in the presence of zinc in ethylene glycol dimethyl ether solvent and the "6β,7β;15β,16β-dimethylene" derivative so obtained was propynylated in position 17 in the presence of potassium ethylate in tetrahydrofuran. Said 17α-(3-hydroxy-1-propynyl)-6β,7β;15β,16β-dimethyleneandrostan-3β,5β,17β-triol was hydrogenated in a mixture of tetrahydrofuran, methanol and pyridine in the presence of Pd/CaCO$_3$ or Pd/C catalyst and the compound obtained was oxidized, lactonized and dehydrated in one step by using chromium trioxide in aqueous pyridine.

According to EP 0,051,143 instead of pivaloyloxy protective group tert-butyl dimethylsilyl, dimethyl-(3-methylbutyl)-silyl or tribenzylsilyl substituent is also suitable.

Beyond that the synthesis consists of 15 steps, the realization thereof at industrial level may go with several problems. In the epoxidation step the use of tert-butyl hydroperoxide in large quantities is dangerous. When zinc dust is applied in a heterogenous system under vigorous stirring a special apparatus is required. The sodium perchlorate is a hazardous material, the carbon tetrachloride as a reactant cannot already be used even at laboratory scale, whereas the potassium ethylate is flammable. Based on experiments, when an ethynyl group is hydrogenated, besides the completely hydrogenated product there are always partially hydrogenated impurities present and said impurities can only be separated with considerable loss of the useful compound either it is a straight chain or cyclic one.

Both the EP 075,189 and the U.S. Pat. No. 4,435,327 patent specifications relate to combined synthetic/microbiological processes. Starting material for the synthesis is, again, the dehydroepiandrosterone which is dihydroxylated by a fermentation process (Colletotrichum phomodies) to give the 3β,7α,15α-trihydroxyandrost-5-en-17-one; the hydroxy substituent in position 7 of said compound is then epimerized by using 35% perchloric acid as catalyst e.g. in a mixture of acetone and dichloro-methane; finally the 3β,7β,15α-trihydroxy derivative is reacted with pivaloyl chloride in pyridine, in the presence of 4-dimethylaminopyridine catalyst to give the 3,15-pivaloylated derivate. An alternative process for the preparation of the compound is also disclosed.

The subsequent steps of the synthesis are the same as those described in EP 051,143.

Besides that this process consists of 12 steps, it uses the reactions mentioned before, which make uncertain a possible industrial application.

In the German patent specification DE 3,626,832 a different novel method for forming the γ-lactone ring is disclosed. The synthesis starts from 15β,16β-methylene-3-methoxy-androsta-3,5-diene-17-one which is reacted with 2-(1-ethoxyethoxy)-3-butenenitrile and the "unsaturated nitrile" derivative obtained is cyclized to form the γ-lactone structure in two steps. Difficulties of this process arise from the synthesis of a special reagent and the bromination in position 6. The use of butyl lithium at industrial scale is not without risk.

According to the German patent specification DE 1,963, 3683(=U.S. Pat. No. 6,121,465) from known intermediates, i.e. from 17α(3-hydroxy-1-propynyl)-6β,7β;15β,16β-bismethylene-androstan-3β,5β,17β-triol and 6β,7β;15β,16β-bismethylene-5β,17β-dihydroxy-3-oxo-17α-pregnane-21-carboxylic acid γ-lactone the drospirenone is prepared by new process. The 17α-(3-hydroxy-1-propynyl)-6β,7β;15β,16β-bismethyleneandrostane-3β,5β,17β-triol is hydrogenated in tetrahydrofuran in the presence of palladium/carbon; the product obtained was used in the next reaction step without further purification.

The "bismethylene propanol" obtained was suspended in acetonitrile, the suspension is heated to 45° C., then 1 mol % of ruthenium trichloride is added in aqueous solution. Subsequently aqueous solution of sodium bromate is added dropwise, the reaction mixture is kept at 50° C. for 2 hours then worked up by extraction method. The 6β,7β;15β,16β-bismethylene-5β,17β-dihydroxy-3-oxo-17α-pregnane-21-carboxylic acid γ-lactone obtained is recrystallized, dehydrated with p-toluenesulfonic acid and purified by chromatography. According to the specification the hydrogenation and oxidation step can be performed with 65-72% yield.

In the European patent EP 0,150,702 a process starting from androst-4ene-3,17-dione is disclosed. The 15α-hydroxy derivative is prepared by a fermentation step, said compound is benzoylated to give an oily product which is reacted with trimethylsulfonium methylide prepared in situ from trimethylsulfonium iodide. From 40 g of 15α-hydroxy-androst-4ene-3,17-dione after purification by chromatography 22.7 g of 15β,16β-methyleneandrost-4-ene-3,17-dione were obtained.

Subsequently a propargyl group was introduced into position 17 by using propargyl alcohol in the presence of potassium ethylate. A compound mixture is obtained in which the double bond of 17β-hydroxy-17α-(3-hydroxy-1-propynyl)-15β,16β-methyleneandrost-5-ene-3-one component is isomerised into the "3-oxo-androst-4-ene" in an additional reaction step. Said "propynyl" derivative is hydrogenated in the presence of tris(triphenylphosphine)rhodium (I) chloride catalyst, formation of the lactone ring is carried out by using chromium trioxide in pyridine. The carbolactone obtained is reacted with orthoformic acid triethyl ester to yield 3-ethoxy-15β,16β-methylene-17α-pregna-3,5-diene-21,17-carbolactone which at position 6 is brominated, the oily product obtained is reacted with lithium bromide and lithium carbonate in dimethylformamide at 100° C. to give the 15β,16β-methylene-3-oxo-17α-pregna-4,6-diene-21,17-carbolactone intermediate after purification by chromatography. Difficulties arising from hydrogenation of propynyl compound and from the bromination at position 6 were discussed above.

According to the German patent specification DE 1,920, 145 3-methoxy-15β,16β-methyleneandrosta-3,5-diene-17-one is synthesized from 15β,16β-methyleneandrosta-4-ene-17-one, which is refluxed with catalytic amount of p-toluenesulfonic acid and 2,2-dimethoxypropane in the presence of methanol in dimethylformamide. Said "3-methoxy" derivative can be used as intermediate for the preparation of drospirenone.

Processes known in the art and realized at laboratory scale can be the source of further unexpected problems when scaling up is carried out. According to recent pharmacopoieal requirements several tests (e.g. TLC or HPLC) are specified to control purity of the drugs which may contain only a limited number of impurities in limited amount. To meet these requirements it is practical to know what impurities and in which amount are present in the intermediates.

Careful analysis of such impurities—particularly in the case of an industrial process—may help to choose the suitable purification methods and to determine which steps can be combined to make the process profitable.

Taking into consideration the above aspects, our aim was to provide a process which can be realized at industrial scale that is safe, lacks the drawbacks of previous processes and by which the drug obtained is pure and meets the pharmacopoieal requirements.

We have surprisingly found that all requirements can be met by the process follows:

the known 15α-hydroxy-androst-4-ene-3,17-dione of the formula (III)

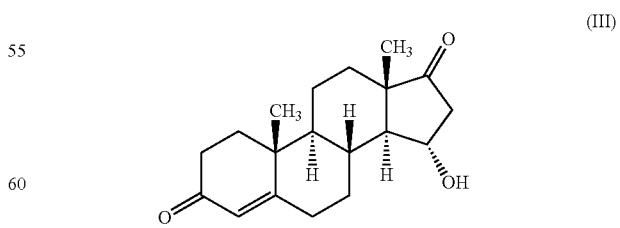

(III)

is esterified on the hydroxy in position 15 with a reactive derivate of a $C_{1-6}$ alkane carboxylic acid to yield a 15α-acyloxyandrost-4-ene-3,17-dione of the general formula (IV),

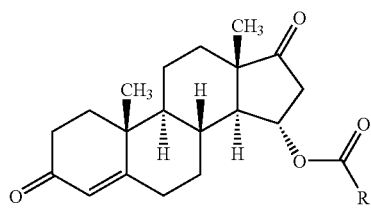

(IV)

wherein R stands for hydrogen atom or an alkyl group having 1-5 carbon atoms-said compound of the general formula (IV) is reacted in the presence of an acidic catalyst with a trialkyl orthoformiate having 1-4 carbon atoms in the alkyl moieties to give 15α-acyloxy-3-alkoxy-androsta-3,5-diene-17-one of the general formula (V),

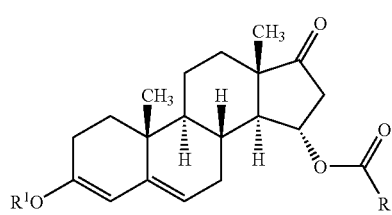

(V)

wherein R has the same meaning as defined above and $R^1$ stands for an alkyl group having 1-4 carbon atoms-said compound of the general formula (V) is reacted with trimethylsulfoxonium methylide prepared in situ in dimethyl sulfoxide from a trimethylsulfoxonium salt and an alkali metal hydroxide to yield 15β,16β-methylene-3-alkoxyandrosta-3,5-diene-17-one of the general formula (VI),

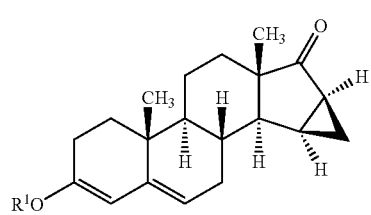

(VI)

wherein $R^1$ has the same meaning as defined above, said compound of the general formula (VI) is reacted in the presence of lithium metal with 2-(2-bromoethyl)-1,3-dioxolane or 2-(2-bromoethyl)-dialkoxy-acetal having 1-4 carbon atoms in the alkoxy moieties, to give 17-hydroxy-15β,16β-methylene-3-alkoxy-17α-pregna-3,5-diene-21-carboxaldehyde cyclic 1,2-ethanediyl-acetal or the 17-hydroxy-15β,16β-methylene-3-alkoxy-17α-pregna-3,5-diene-21-carboxaldehyde dialkoxyacetal of general formula (VII)

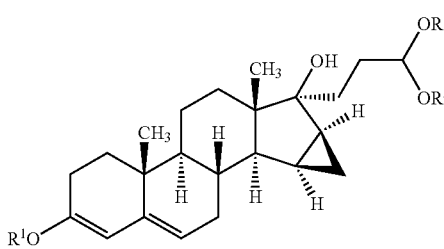

(VII)

wherein $R^1$ has the same meaning as defined above and $R^2$ and $R^3$ stand for an alkyl group having 1-4 carbon atoms or form together a 1,2-ethylene group-said compound of the general formula (VII) is oxidized with chloranil (2,3,5,6-tetrachloro-2,5-cyclohexadiene-1,4-dione) to form 17-hydroxy-15β,16β-methylene-3-oxo-17α-pregna-4,6-diene-21-carboxaldehyde cyclic 1,2-ethanediyl-acetal or 17α-hydroxy-15β,16β-methylene-3-oxo-17α-pregna-4,6-diene-21-carboxaldehyde dialkoxy-acetal of the general formula (VIII)

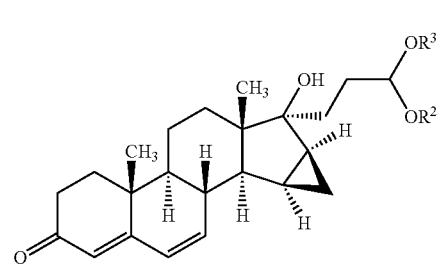

(VIII)

wherein $R^2$ and $R^3$ have the same meaning as defined above-said compound of the general formula (VIII)

a) is cyclized in acidic medium to form 15β,16β-methylene-3-oxo-androsta-4,6-diene-[17(β-1)spiro5']-perhydrofuran-2'ξ-ol-alkyl ether of the general formula (IX)

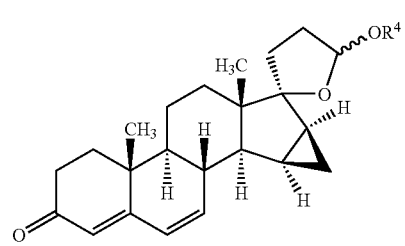

(IX)

wherein $R^4$ stands for methyl, ethyl or propyl group and the ~ bond represents α and β configuration—, and said compound of the formula (IX) is reacted with trimethylsulfoxonium methylide prepared in situ in dimethyl sulfoxide from a trimethylsulfoxonium salt and an alkali metal hydroxide, or b) is reacted with trimethylsulfoxonium methylide prepared in situ in dimethyl sulfoxide from a trimethylsulfoxonium salt and an alkali metal hydroxide to give a bismethylene derivative of the general formula (IXa)

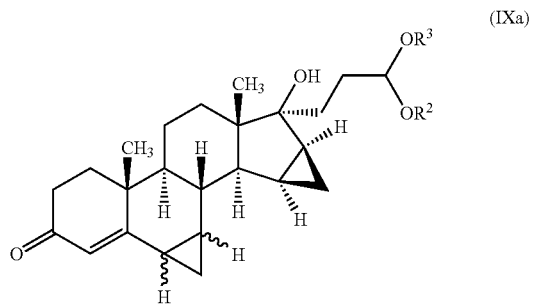

(IXa)

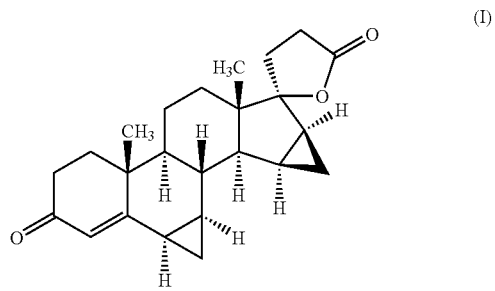

(I)

wherein R² and R³ have the same meaning as defined above and the ~ bond represents α and β configuration-, and said compound of the general formula (IXa) is cyclized in acidic medium,
then from the 6ξ,7ξ;15β,16β-bismethylene-3-oxo-androst-4-ene-[17(β-1)spiro5']-perhydrofuran-2'ε-ol-alkyl ether mixture of the general formula (X) obtained at the end in any of the above alternative step sequences obtained by any of the above synthesis routes is purified by crystallization.

The known starting material for the process according to the invention (i.e. 15α-hydroxy-androst-4-ene-3,17-dione of the formula (III)) suitably is prepared from androst-4-ene-3,17-dione of the formula (II) via microbiological hydroxylation.

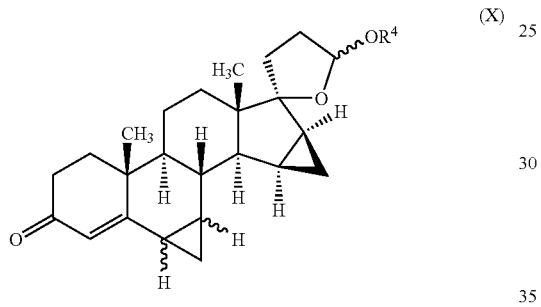

(X)

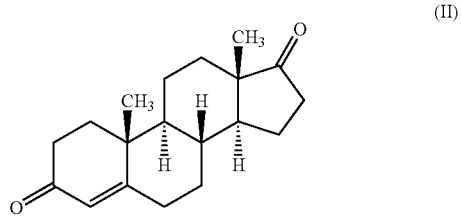

(II)

wherein R⁴ stands for methyl, ethyl or propyl group and the ~bond represents α and β configuration,-
the 6β,7β-isomer is separated by chromatography and is oxidized with Jones-reagent to give the drospirenone, or
the 6ξ,7ξ;15β,16β-bismethylene-3-oxo-androst-4-ene-[17(β-1)spiro5']-perhydrofuran-2'ξ-ol-alkyl ether mixture of the general formula (X) obtained at the end in any of the above alternative step sequences
-wherein R⁴ stands for methyl, ethyl or propyl group and the ~bond represents α and β configuration,- is oxidized with Jones reagent to give 6ξ,7ξ;15β,16β-bismethylene-3-oxo-androst-4-ene-[17(β-1)spiro5']-perhydrofuran-2'-one(17-hydroxy-6ξ,7ξ;15β,16β-bismethylene-3-oxo-17α-pregn-4-ene-21-carboxylic acid γ-lactone) of the general formula (XI)

According to this invention the 15α-hydroxy-androst-4-ene-3,17-dione of the formula (III) preferably is reacted with acetic anhydride in dry tetrahydrofuran in the presence of 4-dimethylaminopyridine below a temperature of 40° C., after the reaction has been completed the reaction mixture is added to water, when the precipitate is dense enough it is filtered, washed until free of mother liquor and dried. The 15α-acetoxy-androst-4-ene-3,7-dione is obtained with 88% yield. The reaction is easy-to-carry out, there are no safety and scale-up problems. The 15α-acetoxy compound obtained can be used in the next reaction step without purification.

The 15α-pivaloyloxy derivative—a novel compound of the general formula (IV), wherein R is a tert-butyl group—can similarly be prepared in pyridine, using 4-dimethylaminopyridine as catalyst and pivaloyl chloride as acylating agent.

The 15α-acyloxy derivatives of the general formula (IV) is then dissolved in dry tetrahydrofuran, the solution is cooled to 0° C. and in the presence of sulfuric acid catalyst is reacted preferably with trimethyl or triethyl orthoformiate. When the reaction is complete, to the solution pyridine is added and the tetrahydrofuran is distilled off using a solvent replacement technique (to acetonitrile), the suspension is filtered and the solid substance is dried. The 15α-acetoxy-3-methoxy-androsta-3,5-diene of the formula (V) is obtained with 95% yield.

The same method is followed when the new 15α-pivaloyloxy-3-methoxy-andosta-3,5-diene-17-one and also when the new 15α-pivaloyloxy-3-ethoxy-androsta-3,5-diene-17-one of the general formula (IV) are prepared.

The 15α-acetoxy-3-methoxy-androsta-3,5-diene-17-one of the general formula (V) is treated with a reagent prepared in situ from trimethylsulfoxonium iodide and potassium hydroxide in a solvent, the reaction mixture is stirred for 6 hours then added to water. The precipitate is filtered off, washed to remove the mother liquor and dried. Finally the

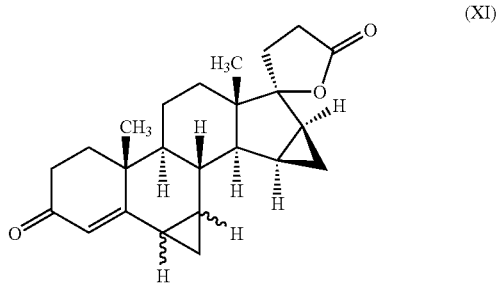

(XI)

wherein the ~ bond represents α and β configuration—and from this isomeric mixture the 6β,7β-isomer is isolated, and if desired the drospirenone of the formula (I)

15β,16β-methylene-3-methoxy-androsta-3,5-diene-17-one obtained (a compound of the general formula (VII)) is crystallized from methanol.

The 15β,16β-methylene-3-ethoxy-andosta-3,5-diene-17-one is prepared by the method described above.

The "3-alkoxy" derivatives of the general formula (VI) formed in the reaction are reacted with 2-(2-bromoethyl)-1,3-dioxolane in dry tetrahydrofuran in the presence of lithium at 0° C. When the reaction is finished the lithium is transformed into lithium hydroxide with a mixture of methanol and water, the solvent is removed by distillation, the residue is mixed with water, the precipitate is filtered, washed to remove the mother liquor, dried and crystallized from methanol. The new compound of the general formula (VII) is obtained with a yield of 92%.

The (17α)-15β,16β-methylene-17-hydroxy-3-methoxy-pregna-3,5-diene-21-carboxaldehyde cyclic 1,2-ethanediyl-acetal, as well as the (17α)-15β,16β-methylene-17-hydroxy-3-methoxy-pregna-3,5-diene-21-carboxaldehyde-diethyl-acetal of the general formula (VII) are also new compounds and are prepared in a manner described above.

Said new "acetals" of the general formula (VII)—of which the (17α)-15β,16β-methylene-17hydroxy-3-methoxy-pregna-3,5-diene-21-carboxaldehyde cyclic 1,2-ethanediyl-acetal is particularly preferred—are dissolved in acetone/water mixture and reacted with chloranil at 25° C. When the reaction is complete, the excess of the chloranil is decomposed with sodium pyrosulfite and the target compound is extracted with dichloromethane. From the extract an oily substance, the (17α)-15β,16β-methylene-17-hydroxy-3-oxo-pregna-4,6-diene-21-carboxaldehyde cyclic 1,2-ethanediyl-acetal of the general formula (VIII) is obtained which in methanol is cyclized with concentrated hydrochloric acid at 0° C. yielding the 15β,16β-methylene-3-oxo-androsta-4,6-diene-[17(β-1')spiro-5']-perhydrofuran-2'ξ-ol-methyl ether (or in a similar manner the "propyl ether") of the general formula (IX).

Said compounds of the general formula (IX) in dimethyl sulfoxide under nitrogen atmosphere are reacted with a reagent in situ prepared from trimethylsulfoxonium iodide and potassium hydroxide. When the reaction is finished, the reaction mixture is diluted with water, the precipitate obtained is filtered, washed until is neutral and dried. The crude product bearing a methylene group of α/β configuration at positions 6,7 and an alkoxy substituent also of two different configuration on the lactol ring, is isolated and is left without further purification.

The alkoxy derivatives of the general formula (X) obtained are reacted in acetone with Jones-reagent at 0-5° C., the excess of the reagent is decomposed by isopropanol and the mixture is added to water. From the aqueous solution the acetone and isopropanol are removed by distillation, the residue is diluted with water and the precipitate is filtered and dried to yield the compound of the general formula (XI). The crude product is dissolved in ethyl acetate, the solution is clarified with activated carbon, then the adsorbent is removed by filtration, the solvent is evaporated. The oily product is first subjected to normal chromatography (normal phase, atmospheric pressure) and then to HPLC to give the separated 6β,7β- and 6α,7α-methylene isomers, respectively.

In another embodiment of the invention the "3-oxo-pregna-4,6-diene" of the general formula (VIII) can be converted into the "bismethylene" derivative of the general formula (X) in such a way that the "diene" of the general formula (VIII) first is treated with a reagent prepared in situ from trimethylsulfoxonium iodide and then the substituents being present in position 17 are cyclized in acidic medium to give the bismethylene compound of the general formula (X).

Separation of the compound of general formula (XI) into the 6β,7β- and 6α,7α-methylene isomers is performed by two-step chromatography: one of them is carried out at atmospheric pressure in normal phase mode (pre-chromatography), the other one is a HPLC method (fine chromatography).

Both in the pre-chromatography and in the fine chromatography silica gel is used as stationary phase and in plant-scale operation a diisopropyl ether/ethyl acetate/dichloromethane mixture of 57:33:10 v/v ratio is used as eluent.

At laboratory scale cyclohexane/ethyl acetate/acetone mixture of the 64:18:18 v/v ratio is also applicable as eluent resulting in the same separation efficiency.

Similar result can be achieved when cyclohexane/ethyl acetate/acetonitrile of the 55:35:10 v/v ratio or cyclohexane/methyl tert-butyl ether/acetone mixture of the 50:30:20 v/v ratio are applied.

Separation of the "β/α" mixture by chromatography is performed with a yield of 50.73%. Description of the pre- and fine chromatography is given in examples 21 and 22.

Further purification of the chromatographed product can be achieved by crystallization from a solvent selected from methanol, ethanol, propanol, isopropanol, ethyl acetate; a solvent mixture containing water up to 10 vol % selected from methanol/water, ethanol/water, propanol/water, isopropanol/water; acetone/diisopropyl ether mixture containing acetone up to 50 vol %; cyclohexane/ethyl acetate mixture containing ethyl acetate up to 50 vol %; dichloromethane/diisopropyl ether mixture containing dichloromethane up to 10 vol %; and dichloromethane/hexane mixture containing dichloromethane up to 10 vol %.

Enclosed is a flow-sheet showing our process in an easy to follow form.

The inventive step of this invention is supported by the following features:

a) A plant-scale process is provided for the synthesis of drospirenone. Published patents and other scientific publications describe laboratory processes. Our process can further be scaled up compared to the batch-size given in the examples.

b) Starting materials for our process, such as the known 15α-hydroxy-androst-4-ene-3,17-dione is readily available being an industrial product.

c) Our process consists of 8 steps, while the other processes known in the art consist e.g. of 15, 12 and 10 steps, respectively.

d) According to this invention also the intermediates are obtained with good yield. E.g. in Example 1. 88%, in Example 3. 95%, in Example 6. 76%, in Example 8. 92%, in Example 11-12. 74%, in Example 15. 65% yield has been achieved.

e) The mixture obtained in the last synthetic step is separated by pre- and fine chromatography with 49.2% yield which is excellent compared with the 16% given in the German patent specification DE 2,652,761.

f) The intermediates obtained in our process are purified by simple crystallization methods. In the other processes, (e.g. in that disclosed in DE 2,652,761) not only the end-product, but also two intermediates are purified by chromatography. In our process in the case of the intermediates disclosed in examples 1, 3, 10 and 14, there was no need for purification.

g) According to the technical literature drospirenone was prepared by using carbon tetrachloride (a prohibited reagent), tert-butylhydroperoxide, sodium hydride, butyllithium, sodium perchlorate and sodium ethylate. These reactants are hazardous materials especially in plant scale applications. The use of zinc requires special apparatus to provide intensive stirring necessary in the case of heterogeneous reactions. Our process is free from such or similar difficulties.

h) Plant-scale production demands intermediates which are easy-to-handle, stable and easy-to-purify. Stability of the (17α)-15β,16β-methylene-17-hydroxy-3-methoxy-pregna-3,5-diene-21-carboxaldehyde cyclic 1,2-ethanediyl-acetal, a specific intermediate of the synthesis, is excellent contrary to other acetals mentioned as applicable in the technical literature.

i) In the case of the preparation of known intermediates any effort has been taken to use easier methods and to achieve better yields in comparison with those described in the technical literature. E.g. the 15α-acetoxy-androst-4-ene-3,17-dione is obtained with a yield of 88% in an easy to reproduce and easy to scale-up way, while in the U.S. Pat. No. 5,236,912 patent specification a yield of 62% is given for this compound.

j) Intermediates and the end-product obtained in our process-particularly with respect to stereochemistry and purity—were carefully analyzed by NMR spectroscopy, the amount of the impurities was determined by HPLC. Regarding intermediates described in the technical literature in most cases there are no such data.

k) Strategically important and specific products of our synthesis are new. Beyond these, several closely related compounds are also novel. The new intermediates are described in examples 2, 4, 5, 8, 9, 10, 11, 14, 15, 16, and 18.

l) We studied in detail the introduction of the "methylene" into the 15α-acyloxy compound to obtain a compound of the general formula (VI) in order to determine the exact reaction parameters. In said reaction dimethyl-[(3-methoxy-17-oxo-androsta-3,5-diene-15β-yl)methyl]sulfonium iodide (VIa) was identified as intermediate which can be transformed into the "15α,16β-methylene" derivative with strict attendance of the temperature. Said intermediate was isolated, its structure was identified, and then was transformed into the 15,16β-compound according to Example 6. We want to remark that we didn't find such studies in the technical literature.

The invention is further illustrated by the following non-limiting Examples.

EXAMPLE 1

5α-Acetoxyandrost-4-ene-3,17-dione 16.9 kg of 15α-hydroxyandrost-4-ene-3,17-dione is suspended in 54 l of dry tetrahydrofuran under vigorous stirring an nitrogen bubbling at room temperature, then 101.4 g of 4-dimethylaminopyridine and 8.45 l of acetic anhydride are added in sequence, while the temperature is kept below 40° C. As the reaction proceeds the mixture becomes clear. After the addition of the acetic anhydride has been finished the mixture is stirred for 30 minutes, then added slowly to 540 l of water and stirred for additional 2 hours, until the precipitate formed becomes dense, filtered by centrifuge, washed with portions of water until it is neutral and dried to constant weight at a temperature below 40° C. The title compound obtained can be used in the next reaction step without further specification.

Yield: 16.9 kg (88%)

Mp: 149-151° C.

$[\alpha]_D^{25}$=+176° (c=1%, ethanol).

$^1$H NMR {500 MHz, CDCl$_3$(TMS), δ(ppm)}: 1.00 (3H,s, 18-Me); 1.05 (1H,m,H-9); 1.22 (3H,d,19-Me); 1.61 (1H,t,H-14); 1.94 (1H,m,H-8); 2.02 & 3.17 (2H,dd & dd,H-16); 2.05 (3H,s, O—CO—CH$_3$); 5.24 (1H,m,H-15); 5.75 (1H,m,H-4).

$^{13}$C NMR {125 MHz, CDCl$_3$(TMS), δ(ppm)}: 15.2 (C-18); 17.5 (C-19); 21.2 (—O—CO—CH$_3$); 35.2 (C-8); 43.4 (C-16); 53.6 (C-9); 53.8 (C-14); 71.6 (C-15); 124.1 (C-4); 169.6 (C-5); 170.7 (—O—CO—CH$_3$); 199.0 (C-3); 214.3 (C-17).

EXAMPLE 2

15α-Pivaloyloxyandrost-4-ene-3,17-dione 8 g (26.45 mmol) of 15α-hydroxyandrost-4-ene-3,17-dione is dissolved in 40 ml of pyridine under nitrogen bubbling and vigorous stirring. To the solution 0.8 g (6.5 mmol) of 4-dimethylaminopyridine is added then 8 ml (64.95 mmol) of pyvaloyl chloride is dropwise added over 8-10 minutes and stirring is continued for 20 hours when the reaction is finished.

During the addition period the temperature of the mixture rises to 30-32° C. After the reaction has been completed the solution is added to 400 ml of water. The precipitate formed is filtered, dissolved in 150 ml of dichloromethane and washed first with 35 ml of 10% hydrochloric acid cooled to 5° C., then with 50 ml of water, 35 ml of 5% sodium bicarbonate solution and again with water (3×50 ml) until it is neutral. The dichloromethane solution is dried (sodium sulfate), filtered, the solvent is removed by distillation. The residue is chromatographed on a column packed with 80 g of silica gel by using a dichloromethane/methanol solvent mixture of increasing polarity as eluent. Fractions containing the title compound are combined, the eluent is removed by distillation and the residue is crystallized from hexane to yield the title compound (6.9 g; 60%).

Mp. 148-150° C.

$[\alpha]_D^{25}$=+159.1° (c=1%, ethanol.

1H NMR {500 MHz, CDCl3(TMS), δ(ppm)}: 1.01 (3H,s, 18-Me); 1.06 (1H,m,H-9); 1.19 (9H,s,—O—CO—C (CH$_3$)$_3$); 1.23 (3H,s,19-Me); 1.63 (1H,m,H-14); 1.92 & 3.19 (2H,m & m,H-16); 1.94 (1H,m,H-8); 5.19 (1H,m,H-15); 5.75 (1H,m,H-4).

$^{13}$C NMR {125 MHz, CDCl3(TMS) δ(ppm)}: 15.3 (C-18); 17.5 (C-19); 27.0 (—O—CO—C(CH$_3$)$_3$), 35.1 (C-8); 38.5 (—O—CO—C(CH$_3$)$_3$); 43.5 (C-16); 53.6 (C-9); 53.9 (C-14); 71.6 (C-15); 124.1 (C-4), 169.6 (C-5); 178.1 (—O—CO—C(CH$_3$)$_3$), 199.0 (C-3); 214.5 (C-17).

EXAMPLE 3

15α-Acetoxy-3-methoxyandrosta-3,5-diene-17-one 16.9 of 15α-acetoxyandrost-4-ene-3,17-dione is dissolved in 101 l of dry tetrahydrofuran under vigorous stirring and nitrogen bubbling at room temperature. The reaction mixture is cooled to 0° C. and 8.04 l of trimethyl orthomormiate and then 1.7 l of tetrahydrofuran containing 1 vol % of sulfrifc acid are added. The reaction mixture is stirred for 5 hours at 0-2° C., at this time 5.4 l of pyridine is added and stirring is continued for 20 minutes. The tetrahydrofuran is removed by distillation while continuously is replaced by acetonitrile and the volume is adjusted to the ⅓ of the original volume. The acetonitrile containing the title compound as a crystal suspension is cooled to 0° C., filtered by centrifuge, the mother liquor is washed away with acetonitril cooled to 0° C. and the product is dried in vacuo to constant weight at temperature of 40° C.

Yield: 16.7 kg (95%)
Mp: 206-211° C.
$[\alpha]_D^{25}$=14° (c=1%, dioxane).
$[\alpha]_D^{25}$=−13.5° (c=0.5%, chloroform).
$^1$H NMR {500 MHz, CDCl$_3$(TMS), δ(ppm)}: 0.99 (3H,s, 18-Me); 1.00 (1H,m,H-9); 1.13 (1H,m,H-9); 1.66 (1H,t,H-14); 2.02 & 3.14 (2H,dd & dd,H-16); 2.05 (1H,m,H-8); 2.07 (3H,s,—O—CO—CH$_3$); 3.58 (3H,s,—O—CH$_3$); 5.13 (1H,m,H-4); 5.20 (1H,m,H-6); 5.26 (1H,m,H-15).
$^{13}$C NMR {125 MHz, CDCl$_3$(TMS), δ(ppm)}: 15.0 (C-18); 19.0 (C-19); 21.2 (—O—CO—CH$_3$); 31.6 (C-8); 43.4 (C-16); 48.0 (C-9); 54.3 (—O—CH$_3$); 54.4 (C-14); 72.2 (C-15); 98.3 (C-4); 117.4 (C-6); 140.5 (C-5); 155.4 (C-3); 170.8 (—O—CO—CH$_3$); 214.9 (C-17).

EXAMPLE 4

15α-Pivaloyloxy-3-methoxyandrosta-3-diene-17-one

Starting from 2 g (5.17 mmol) of 15α-pivaloyloxyandrost-4-ene-3,17-dione 1.53 g (73.8%) of the title compound is obtained in a manner described in example 3.
Mp: 217-222° C.
$[\alpha]_D^{25}$=+3.79° (c=1, chloroform).
$^1$H NMR {500 MHz, CDCl$_3$(TMS), δ(ppm)}: 1.00 (3H,s, 18-Me); 1.00 (1H,m,H-9); 1.14 (1H,m,H-9); 1.20 (9H,s,—O—CO—C(CH$_3$)$_3$); 1.68 (1H,t,H-14); 1.93 & 3.17 (2H,m & m,H-16); 2.05 (1H,m,H-8); 3.57 (3H,s,—O—CH$_3$); 5.12 (1H,m,H-4); 5.20 (1H,m,H-15); 5.21 (1H,m,H-6).
$^{13}$C NMR {125 MHz, CDCl$_3$(TMS), δ(ppm)}: 15.1 (C-18); 19.0 (C-19); 27.1 (—O—CO—C(CH$_3$)$_3$); 31.5 (C-8); 38.5 (—O—CO—C(CH$_3$)$_3$); 43.5 (C-16); 48.0 (C-9); 54.3 (—O—CH$_3$); 54.4 (C-14); 72.2 (C-15); 98.3 (C-4); 117.3 (C-6); 140.5 (C-5); 155.4 (C-3); 178.2 (—O—CO—C(CH$_3$)$_3$); 215.1 (C-17).

EXAMPLE 5

15α-Acetoxy-3-ethoxyandrosta-3,5-diene-17-one

Starting from 22.5 g (65.32 mmol) of 5α-acetoxyandrost-4-ene-3,17-dione the compound is prepared according to Example 3, with the alteration that instead of trimethyl orthofomiate triethyl orthoformiate is used. The title compound is crystallized from acetonitrile.
Yield: 21.8 g (89.7%)
Mp: 183-187° C.
$[\alpha]_D^{25}$=−11.43° (c=1%, chloroform.
$^1$H NMR {500 MHz, CDCl$_3$(TMS), δ(ppm)}: 0.98 (3H,s, 18-Me); 1.00 (3H,s,19-Me); 1.13 (1H,m,H-9); 1.30 (3H,t,—O—CH$_2$—CH$_3$); 1.66 (1H,m,H-14); 2.02 & 3.14 (2H,m & m,H-16); 2.05 (1H,m,H-8); 2.06 (3H,s,—O—CO—CH$_3$); 3.78 (2H,m,—O—CH$_2$—CH$_3$); 5.11 (1H,m,H-4); 5.17 (1H,m,H-6); 5.26 (1H,m,H-15).
$^{13}$C NMR {125 MHz, CDCl$_3$(TMS), δ(ppm)}: 14.7 (—O—CH$_2$—CH$_3$): 15.0 (C-18); 19.0 (C-19); 21.2 (—O—CO—CH$_3$); 43.4 (C-16); 31.6 (C-8); 48.0 (C-9); 54.4 (C-14); 62.2 (—O—CH$_2$—CH$_3$); 72.2 (C-15); 98.8 (C-4); 117.0 (C-6); 140.7 (C-5); 154.6 (C-3); 170.8 (—O—CO—CH$_3$); 215.0 (C-17).

EXAMPLE 6

15β,16β-Methylene-3-methoxyandrosta-3,5-diene-17-one 12.96 kg of trimethylsulfoxonium iodide is dissolved in 180 l of dimethyl sulfoxide under nitrogen bubbling and vigorous stirring and at 25-30° C. 5.51 kg of potassium hydroxide is added to the solution. Stirring is continued for 1 hour, then 16.22 kg of 15α-acetoxy-3-methoxyandrosta-3,5-diene-17-one is added, the reaction mixture is stirred at 25-30° C. until the reaction is complete (about 6 hours). The solution is added slowly to 900 l of water, the precipitate obtained is stirred for 30 minutes until it is dense, filtered by centrifuge, washed with portions of water until is neutral and dried in vacuo to constant weight at a temperature below 40° C. and the crude tide compound is crystallized from methanol.
Yield: 10.76 kg (76%)
Mp: 159-161° C.
$[\alpha]_D^{25}$=−177.6° (c=1, dioxane).
$^1$H NMR {125 MHz, CDCl$_3$(TMS), δ(ppm)}: 1.00 (6H,s, 18-Me & 19-Me); 1.12 & 1.64 (2H,m & m,CP(15β,16β)(CH$_2$)); 1.15 (1H,m,H-9); 1.74 (1H,m,H-16); 1.97 (1H,m,H-15); 1.98 (1H,m,H-8); 2.00 (1H,m,H-14); 3.58 (3H,m,—O—CH$_3$); 5.16 (1H,d,H-4); 5.29 (1H,m,H-6).
$^{13}$C NMR {125 MHz, CDCl$_3$(TMS), δ(ppm)}: 17.1 (CP (15β,16β)(CH$_2$)); 18.9 (C-19); 20.1 (C-18); 22.1 (C-15); 25.8 (C-16); 30.4 (C-8); 49.3 (C-9); 52.4 (C-14); 54.3 (—O—CH$_3$); 98.4 (C-4); 117.3 (C-6); 141.5 (C-5); 155.5 (C-3); 216.5 (C-17).
From the mother liquor of the crystallization dimethyl-[(3-methoxy-17-oxandrosta-3,5-diene-15β-yl)methyl]sulfoxonium iodide, the intermediate of the reaction can be isolated.
Mp: 179-181° C.
$^1$H NMR {500 MHz, CDCl$_3$:DMSO-d$_6$(TMS) 1:1, δ (ppm)}: 0.99 (3H,s,18-Me); 1.01 (3H,s,H-19); 1.17 (1H,m, H-9); 1.84 (1H,m,H-14); 1.98 (1H,m,H-8); 2.60 & 2.70 (2H, dd & dd,H-16); 3.12 (1H,m,H-15); 3.54 (3H,s,—O—CH$_3$); 3.89 & 3.91 (6H,s & s,—CH$_2$—(S$^+$O)(CH$_3$)$_2$); 4.30 & 4.42 (2H,d & dd,—CH$_2$—(S$^+$O)(CH$_3$)$_2$); 5.13 (1H,m,H-4); 5.19 (1H,m,H-6).
$^{13}$C NMR {125 MHz, CDCl$_3$:DMSO-d$_6$(TMS) 1:1 (TMS), δ (ppm)}: 16.1 (C-18); 18.6 (C-19); 25.9 (C-15); 28.3 (C-8); 37.2 & 37.4 (—CH$_2$—(S$^+$O)(CH$_3$)$_2$); 42.3 (C-9); 52.7 (,—CH$_2$—(S$^+$O)(CH$_3$)$_2$)); 53.7 (C-14); 54.0 (—O—CH$_3$); 98.0 (C-4); 116.5 (C-6); 140.8 (C-5); 155.2 (C-3); 216.9 (C-17).
This intermediate can be converted into the 15β,16β-methylene-3-methoxyandrosta-3,5-diene-17-one in the following manner: 1.6 g of trimethylsulfoxonium iodide is dissolved in 22 ml of dimethyl sulfoxide under nitrogen atmosphere with vigorous stirring, then 0.68 g of potassium hydroxide is added at 25-30° C. The reaction mixture is stirred for additional 1 hour, then 2 g (3.74 mmol) dimethyl-[(3-methoxy-17-oxandrosta-3,5-diene-15β-yl)methyl]sulfoxonium iodide is added and stirring is continued at 25-30° C. until the reaction is finished (about 4 hours). The solution is slowly added to 110 ml of water, stirred for 30 minutes until the precipitate is dense, filtered, washed with portions of water until neutral and dried in vacuo to constant weight at a temperature below 40° C. The crude title compound is crystallized from methanol.
Yield: 0.95 g (84.2%)
Physical parameters are the same as given above.

EXAMPLE 6/a

15β,16β-Methylene-3-methoxyandrosta-3,5-diene-17-one

Starting from 5 g (12.93 mmol) of 15α-pivaloyloxy-3-methoxyandrosta-3,5-diene-17-one 2.6 g (65%) of the title compound is prepared in a manner described in Example 6.
Physical characteristics are the same as given in Example 6.

EXAMPLE 7

15β,16β-Methylene-3-ethoxyandrosta-3,5-diene-17-one

Starting from 20 g of 15α-acetoxy-3-ethoxyandrosta-3,5-diene 16.75 g (65%) of the crude title compound is obtained in a manner described Example 6, and is crystallized from 200 ml of ethanol containing 0.2 ml of pyridine.

Yield: 12.98 g (74.5%)

Mp: 159-162° C.

$[\alpha]_D^{25}$=−178.6° (c=1 dioxane).

$^1$H NMR {500 MHz, CDCl$_3$(TMS), δ(ppm)}: 1.00 (3H,s, 18-Me); 1.01 (3H,d,19-Me); 1.11 & 1.63 (2H,m & m,CP (15β,16β)(CH$_2$)); 1.14 (1H,m,H-9); 1.31 (3H,t,—O—CH$_2$—C$_3$); 1.74 (1H,m,H-16); 1.97 (1H,m,H-15); 1.98 (1H,m,H-8); 2.00 (1H,m,H-14); 3.78 (2H,m,—O—CH$_2$—CH$_3$); 5.14 (1H,d,H-4); 5.26 (1H,m,H-6).

$^{13}$C NMR {125 MHz, CDCl$_3$(TMS), δ(ppm)}: 14.6 (—O—CH$_2$—CH$_3$); 17.1 (CP(15β,16β)(CH$_2$)); 18.9 (C-19); 20.0 (C-18); 22.1 (C-15); 25.8 (C-16); 30.4 (C-8); 49.3 (C-9); 52.4 (C-14); 62.2 (—O—CH$_2$—CH$_3$); 98.9 (C-4); 117.0 (C-6); 141.7 (C-5); 154.7 (C-3); 216.5 (C-17).

EXAMPLE 8

17-Hydroxy-15β,16β-methylene-3-methoxy-17α-pregna-3,5-diene-21-carboxaldehyde cyclic 1,2ethanediyl acetal 10.5 kg of 15β,16β-methylene-3-methoxyandrosta-3,5-diene-17-one is dissolved in 147 l of dry tetrahydrofuran under vigorous stirring in argon atmosphere at room temperature. The solution is cooled to 0° C. and 1.89 kg of lithium metal is added. To the solution 12.6 l of 2-(2-bromoethyl)-1,3-dioxolane is added under intensive stirring and cooling at a temperature of 10-20° C. Stirring at 15-20° C. is continued for 5 hours, then the excess of lithium is decomposed with 10 l of methanol and 100 of water to form lithium hydroxide. After the complete decomposition the methanol and tetrahydrofuran are distilled off, to the residue 80 l of water is added. When the precipitate is dense enough it is filtered, washed with portions of water to neutral and dried in vacuo to constant weight at a temperature below 40° C. to give 13.8 kg of crude title compound which is crystallized from methanol.

Yield: 12.87 kg (92%)

Mp: 164-166° C.

$[\alpha]_D^{25}$=−141.3° (c=1, dioxane).

1H NMR {500 MHz, CDCl$_3$(TMS), δ(ppm)}: 0.24 & 1.00 (2H,m & m,CP(15β,16β)(CH$_2$)); 0.95 (3H,s,18-Me); 1.00 (3H,s,19-Me); 1.06 (1H,m,H-9); 1.19 (1H,m,H-15); 1.32 (1H,m,H-16); 1.66 & 1.75 (2H,m & m,H-20); 1.69 (1H,m,H-14); 1.88 (H-1,m,H-8); 1.94 &2.06 (2H,m & m,H-21); 3.58 (3H,m, —O—CH$_3$); 3.87 & 4.00 (4H,m & m,2×—O—CH$_2$—); 4.94 (1H,t,H-22), 5.15 (1H,m,H-4); 5.27 (1H,m,H-6).

$^{13}$C NMR {125 MHz, CDCl$_3$(TMS), δ(ppm)}: 7.4 (CP (15β,16β)(CH$_2$)); 16.0 (C-15): 18.9 (C-19); 19.4 (C-18); 23.0 (C-16); 28.4 (C-21); 30.9 (C-20); 31.3 (C-8); 49.0 (C-9); 53.2 (C-14); 54.3 (—O—CH$_3$); 64.96 & 64.99(2×—O—CH$_2$—); 82.2 (C-17); 98.6 (C-4); 105.1 (C-22); 118.1 (C-6); 141.2 (C-5); 155.4 (C-3).

EXAMPLE 9

17-Hydroxy-15β,16β-methylene-3-ethoxy-17α-pregna-3,5-diene-21-carboxaldehyde cyclic 1,2-ethanediyl acetal Starting from 10 g of 3-ethoxy-15β,16β-methyleneandrosta-3,5-diene-17-one the title compound is prepared according to Example 8, with the alteration that after the reaction has been completed the oily product precipitated from the aqueous solution is extracted with 100 ml of dichloromethane, the organic layer is washed with water to neutral, dried (sodium sulfate) and filtered. From the filtrate the dichloromethane is distilled off and the residue is crystallized from methanol to yield 11.02 g of the title compound.

Yield: 11.02 g (83%)

Mp: 66-68° C.

$[\alpha]_D^{25}$=−132.6° (c=1 dioxane).

$^1$H NMR {500 MHz, CDCl$_3$(TMS), δ(ppm)}: 0.24 & 1.00 (2H,m & m,CP(15β,16β)(CH$_2$)); 0.95 (3H,s,18-Me); 1.00 (3H,s,19-Me); 1.06 (1H,m,H-9); 1.19 (1H,m,H-15); 1.30 (3H,t, —O—CH$_2$—CH$_3$); 1.33 (1H,m,H-16); 1.65 & 1.74 (2H,m & m,H-20); 1.69 (1H,m,H-14); 1.87 (H-1,m,H-8); 1.94 & 2.06 (2H,m & m,H-21); 3.78 (2H,m, —O—CH$_2$—CH$_3$); 3.87 & 4.00 (4H,m & m,2×—O—CH$_2$—); 4.94 (1H, t,H-22); 5.13 (1H,m,H-4); 5.24 (1H,m,H-6).

$^{13}$C NMR {125 MHz, CDCl$_3$(TMS), δ(ppm)}: 7.4 (CP (15β,16β)(CH$_2$)); 14.7 (—O—CH$_2$—CH$_3$); 16.0 (C-15): 18.9 (C-19); 19.3 (C-18); 23.0 (C-16); 28.4 (C-21); 30.9 (C-20); 31.3 (C-8); 49.0 (C-9); 53.2 (C-14); 62.2 (—O—CH$_2$—CH$_3$); 64.96 & 64.99(2×—O—CH$_2$—); 82.2 (C-17); 99.1 (C-4); 105.1 (C-22); 117.8 (C-6); 141.4 (C-5); 154.5 (C-3).

EXAMPLE 10

17-Hydroxy-15β,16β-methylene-3-methoxy-17α-pregna-3,5-diene-21-carboxaldehyde-diethyl-acetal The title compound is prepared from 10 g of 15β,16β-methylene-3-methoxyandrosta-3,5-diene-17-one and 12 ml of 3-chloropropionaldehyde diethyl acetal in a manner described in Example 9 with a yield of 10.17 g (77%).

Mp: 46-48° C.

$[\alpha]_D^{25}$=−141.3° (c=1 dioxane).

$^1$H NMR {500 MHz, DMSO-d$_6$(TMS), δ(ppm)}: 0.13 & 0.86 (2H,m & m,CP(15β,16β)(CH$_2$)); 0.84 (3H,s,18-Me); 0.92 (3H,s,19-Me); 0.99 (1H,m,H-9); 1.07 (1H,m,H-15); 1.11 (6H,t,—O—CH$_2$—CH$_3$); 1.17 (1H,m,H-16); 1.40 & 1.49 (2H,m & m,H-20); 1.59 (1H,m,H-14); 1.72 & 1.82 (2H,m & m,H-21); 1.78 (H-1,m,H-8); 3.43 & 3.57 (4H,m & m, —O—CH$_2$—CH$_3$); 3.49 (3H,m, —O—CH$_3$); 4.12 (1H, s,—OH); 4.45 (1H,t,H-22); 5.14 (1H,m,H-4); 5.20 (1H,m,H-6).

$^{13}$C NMR {125 MHz, DMSO-d$_6$(TMS), δ(ppm)}: 7.3 (CP (15β,16β)(CH$_2$)); 15.27 (C-15): 15.31 (2×—O—CH$_2$—CH$_3$); 18.5 (C-19); 19.3 (C-18); 22.3 (C-16); 28.1 (C-21); 30.9 (C-8); 31.8 (C-20); 48.4 (C-9); 52.7 (C-14); 53.9 (—O—CH$_3$); 60.2 & 60.4 (2×—O—CH$_2$—CH$_3$); 80.5 (C-17); 98.5 (C-4); 103.2 (C-22); 117.6 (C-6); 140.4 (C-5);154.5 (C-3).

EXAMPLE 11

17-Hydroxy-15β,16β-methylene-3-oxo-17α-pregna-4,6-diene-21-carboxaldehyde cyclic 1,2-ethanediyl-acetal 12.8 kg of 17-hydroxy-15β,16β-methylene-3-methoxy-17α-pregna-3,5-diene-21-carboxaldehyde cyclic 1,2- ethanediyl acetal is dissolved in 345 l of acetone under vigorous stirring in nitrogen atmosphere at room temperature, then 42 l of water and 8.4 kg of chloranil are added to the suspension and the reaction mixture is stirred at 25° C. To the solution obtained 400 l of 5% aqueous sodium pyrosulfite solution is added, the mixture is stirred for 0.5 hour and the acetone is removed by distillation. The residue is extracted with 265 l of dichloromethane, the organic layer is washed with 60 l of 10% aqueous sodium hydroxide solution and twice with 50 l of water in sequence (until neutral). The dichloromethane solution is dried on sodium sulfate, the drying agent is removed by filtration and from the filtrate the dichloromethane is evaporated. To the residue 25 l of methanol is added and then is distilled off, yielding 12.2 kg of oily title compound which can be used in the next reaction step without purification.

The oily product can be crystallized from isopropanol giving the product with the following physical characteristics:

Mp: 142-144° C.

$[\alpha]_D^{25}$=+89.7° (c=1%, chloroform).

$^1$H NMR {500 MHz, CDCl$_3$(TMS), δ(ppm)}: 0.36 & 1.09 (2H,m & m,CP(15β,16β)(CH$_2$)); 1.01 (3H,s,18-Me); 1.13 (3H,s,19-Me); 1.25 (1H,m,H-9); 1.34 (1H,m,H-15); 1.40 (1H,m,H-16); 1.64 & 1.76 (2H,m & m,H-20); 1.84 (1H,m,H-14); 1.95 & 2.06 (2H,m & m,H-21); 2.43 (H-1,m,H-8); 3.87 & 3.99 (4H,m & m,2×—O—CH$_2$—); 4.93 (1H,t,H-22); 5.69 (1H,m,H-4); 6.16 (1H,m,H-6); 6.37 (1H,m,H-7).

$^{13}$C NMR {125 MHz, CDCl$_3$(TMS), δ(ppm)}: 7.9 (CP(15β,16β)(CH$_2$)); 15.5 (C-15); 16.3 (C-19); 19.3 (C-18); 23.3 (C-16); 28.3 (C-21); 30.8 (C-20); 37.0 (C-8); 50.5 (C-14; 51.4 (C-9); 64.98 & 65.00 (2×—O—CH$_2$—); 81.9 (C-17); 104.9 (C-22); 123.8 (C-4); 128.1 (C-6); 141.0 (C-7); 163.8 (C-5); 199.5 (C-3).

EXAMPLE 12

15β,16β-Methylene-3-oxo-androsta-4,6-diene[17(β-1')spiro-5']-perhydrofuran-2'ξ-ol-methyl ether 12.2 kg of the oily product obtained in Example 11, is dissolved in 76 l of methanol, cooled to 0° C. and under continuous cooling 30.5 l of concentrated hydrochloric acid is added at 0° C. The mixture is stirred for 1 hour, tie precipitate formed is filtered, washed with portions of water until is free of acid and dried in vacuo to constant weight at a temperature below 40° C., to give 9.1 kg of the title compound which is crystallized from methanol.

Cumulated yield of the Examples 11 and 12 is 8.4 kg (74%)

Mp: 142-144° C.

$[\alpha]_D^{25}$=+95° (c=0.5%, CHCl$_3$).

$^1$H NMR {500 MHz, CDCl$_3$(TMS), δ(ppm)}: 0.42 & 1.17 (2H,m & m,CP(15β,16β)(CH$_2$)); 1.04 (3H,s,18-Me); 1.13 (3H,s,19-Me); 1.20 (1H,m,H-16); 1.25 (1H,m,H-9); 1.36 (1H,m,H-15); 1.68 & 2.24 (2H,m & m,H-20); 1.74 (1H,m,H-14); 1.86 & 2.19 (2H,m & m,H-21); 2.43 (H-1m,H-8); 3.34 (3H,s,—O—CH$_3$); 5.05 (1H,m,H-22); 5.69 (1H,m,H-4); 6.17 (1H,m,H-6); 6.39 (1H,m,H-7).

$^{13}$NMR {125 MHz, CDCl$_3$(TMS), δ(ppm)}: 8.9 (CP(15β,16β)(CH$_2$)); 14.9 (C-15); 16.3 (C-19); 20.3 (C-18); 25.3 (C-16); 31.7 (C-20); 32.7 (C-21); 36.9 (C-8); 50.9 (C-14); 51.2 (C-9); 55.0 (—O—CH$_3$); 94.5 (C-17); 105.0 (C-22); 123.8 (C-4); 128.1 (C-6); 140.9 (C-7); 163.8 (C-5); 199.5 (C-3).

EXAMPLE 13

15β,16β-methylene-3-oxo-androsta-4,6-diene-[17(β-1')spiro-5']-perhydrofuran-2'ξ-methyl ether (Reaction Route 2)

Starting from 6.0 g of (17α)-15β,16β-methylene-17-hydroxy-3-methoxy-pregna-3,5-diene-21-carboxaldehyde-diethyl-acetal the compound is prepared according to Examples 11 and 12, with the alteration that the 17-hydroxy-15β,16β-methylene-3-oxo-17α-pregna-4,6-diene-21-carboxaldehyde cyclic 1,2-ethanediyl-acetal obtained by chloranil oxidation of enol-ether, is not isolated in pure form.

Yield: 3.20 g (65%)

EXAMPLE 14

15β,16β-methylene-3-oxo-androsta-4,6-diene-[17(β-1')spiro-5']-perhydrofuran-2'ξ-ol-propyl ether Starting from 8.9 g of 17-hydroxy-15β,16β-methylene-3-oxo-17α-pregna-4,6-diene-21-carboxaldehyde cyclic 1,2-ethanediyl-acetal the method described in Example 12 is followed with the alteration that instead of methanol n-propanol is used and at the work-up stage the n-propanol is removed by distillation. The residue is extracted with 100 ml of dichloromethane, the organic phase is washed to neutral with 2×50 ml of water. The dichloromethane layer is dried on sodium sulfate, the drying agent is removed by filtration, from the filtrate the solvent is distilled off and the residue is chromatographed on 80 g of silica gel and is eluted from the column with dichloromethane. Fractions containing the title compound are combined, the eluent is distilled off to give 5.63 g (58%) of the oily title compound, which is used in the next step without crystallization. The product is a mixture of two compounds in a ratio of 3:2 and differ in the configuration of the propyl group.

$^1$H NMR {500 MHz, CDCl$_3$(TMS), δ(ppm)[major/minor]}: 0.41 & 1.17/0.38 & 1.15 (2H,m & m,CP(15β,16β)(CH$_2$)); 0.91/0.94 (3H,t,—O—CH$_2$13 CH$_2$—CH$_3$); 1.03/1.00 (3H,s,18-Me); 1.131/1.127 (3H,s,19-Me); 1.19/1.28 (1H,m,H-16); 1.24 (1H,m,H-9); 1.35 (1H,m,H-15); 1.57/1.62 (2H,m,—O—CH$_2$—CH$_2$—CH$_3$); 1.67 & 2.25/1.89 & 2.04 (2H,m & m,H-20); 1.74/1.67 (1H,m,H-14); 1.87 & 2.18/1.84 & 1.95 (2H,m & m,H-21); 2.42/2.39 (H-1,m,H-8); 3.33 & 3.65/3.38 & 3.73 (2H,m,—O—CH$_2$—CH$_2$—CH$_3$); 5.15/5.08 (1H,m,H-22); 5.69 (1H,m,H-4); 6.17 (1H,m,H-6); 6.39 (1H,m,H-7).

$^{13}$NMR {125 MHz, CDCl$_3$(TMS), δ(ppm)[major/minor]}: 8.9/9.4 (CP(15β,16β)(CH$_2$)); 10.84/10.80 (—O—CH$_2$—CH$_2$—CH$_3$); 14.9/15.1 (C-15); 16.26/16.29 (C-19); 20.3/19.8 (C-18); 23.0/23.1 (—O—CH$_2$—CH$_2$—CH$_3$); 25.4/26.6 (C-16); 31.9/31.8 (C-20); 32.7/32.9 (C-21); 36.94/36.79 (C-8); 51.0/50.2 (C-14); 51.2/51.3 (C-9); 69.4/68.7 (—O—CH$_2$—CH$_2$—CH$_3$); 94.3/93.6 (C-17); 103.7/103.0 (C-22); 123.75/123.74 (C-4); 128.13/128.08 (C-6); 140.97/141.06 (C-7); 163.83/163.82 (C-5); 199.45/199.41 (C-3).

EXAMPLE 15

6ξ,7ξ;15β,16β-Bismethylene-3-oxo-androst-4-ene-[17(β-1')spiro-5']-perhydrofuran-2'ξ-ol-methyl ether 19.41 kg of trimethylsulfoxonium iodide is suspended in 162 l of dry dimethyl sulfoxide under nitrogen with vigorous stirring at room temperature, then 4.94 kg of potassium hydroxide is added and stirring is continued for 1 hour. To this reagent prepared in situ 8.14 kg of 15β,16β-methylene-3- oxo-androsta-4,6-diene-[17(β-1')spiro-5']-perhydrofuran-2'ξ-ol-methyl ether is added and the mixture is stirred for 20 hours at 25° C. The mixture is added to 810 l of water and the mixture containing the precipitated product is stirred for 30 minutes, filtered by centrifuge, washed until is neutral with portions of water and dried in vacuo to constant weight at a temperature below 40° C. The product obtained is a mixture of the 6β,7β- and 6α,7α-isomers of the title compound, wherein the amount of the 6β,7β-isomer is 65%.

Yield: 8.07 kg

NMR-assignation of the 6β,7β-isomer in the mixture:
$^1$H NMR {500 MHz, CDCl$_3$(TMS), δ(ppm)}: 0.40 & 1.18 (2H,m & m,CP(15β,16β)(CH$_2$)); 0.87 & 1.21 (2H,m & m,CP(6β,7β)(CH$_2$)); 0.97 (3H,s,18-Me); 1.10 (3H,d,19-Me); 1.10 (1H,m,H-9); 1.20 (1H,m,H-16); 1.42 (1H,m,H-15); 1.51 (1H,m,H-7); 1.62 (1H,m,H-6); 1.68 & 2.24 (2H,m & m,H-20); 1.76 (1H,m,H-8); 1.86 & 2.19 (2H,m & m,H-21); 1.86 (1H,m,H-14); 3.335 (3H,s,—O—CH$_3$); 5.05 (1H,m,H-22); 6.02 (1H,m,H-4).

$^{13}$C NMR {125 MHz, CDCl$_3$(TMS), δ(ppm)}: 8.9 (CP(15β,16β)(CH$_2$)); 15.5 (C-15): 17.6 (C-19); 18.9 (CP(6β,7β)(CH$_2$)); 19.1 (C-6); 20.1 (C-7); 20.2 (C-18); 25.1 (C-16); 31.7 (C-20); 32.69 (C-21); 34.7 (C-8); 51.9 (C-9); 53.1 (C-14); 54.97 (—O—CH$_3$); 94.5 (C-17); 104.91 (C-22); 125.7 (C-4); 172.0 (C-5); 198.0 (C-3).

NMR-assignation of the 6α,7α-isomer in the mixture:
$^1$H NMR {500 MHz, CDCl$_3$(TMS), δ(ppm)}: 0.37 & 1.16 (2H,m & m,CP(15β,16β)(CH$_2$)); 0.58 & 0.92 (2H,m & m,CP(6β,7β)(CH$_2$)); 0.79 (1H,m,H-9); 1.03 (3H,s,18-Me); 1.15 (3H,d,19-Me); 1.16 (1H,m,H-16); 1.36 (1H,m,H-15); 1.52 (1H,m,H-7); 1.63 (1H,m,H-14); 1.68 & 2.24 (2H,m & m,H-20); 1.79 (1H,m,H-6); 1.86 & 2.19 (2H,m & m,H-21); 2.22 (1H,m,H-8); 3.338 (3H,s,—O—CH$_3$); 5.04 (1H,m,H-22); 5.96 (1H,m,H-4).

$^{13}$C NMR {125 MHz, CDCl$_3$(TMS), δ(ppm)}: 8.66 (CP(15β,16β)(CH$_2$)); 8.69 (CP(6α,7α)(CH$_2$)); 14.9 (C-7); 15.2 (C-15); 15.8 (C-6); 17.2 (C-19); 20.6 (C-18); 25.0 (C-16); 30.7 (C-8); 31.75 (C-20); 32.68 (C-21); 41.9 (C-9); 51.8 (C-14); 55.0 (—O—CH$_3$); 94.7 (C-17); 104.86 (C-22); 126.6 (C-4); 172.5 (C-5); 198.1 (C-3).

Since the methyl ether on the lactol ring may have α- or β-configuration and similarly the methylene ring in positions 6,7 may have α- or β-arrangement, four isomers were obtained which were separated by preparative HPLC.

NMR data of pure 6β,7β;15β,16β-bismethylene-3-oxo-androst-4-ene-[17(β-1')spiro-5']-perhydrofuran-2'ξ-ol-methyl ether:
$^1$H NMR {500 MHz, CDCl$_3$(TMS), δ(ppm)}: 0.40 & 1.18 (2H,m & m,CP(15β,16β)(CH$_2$)); 0.86 & 1.21 (2H,m & m,CP(6β,7β(CH$_2$)); 0.97 (3H,s,18-Me); 1.10 (3H,d,19-Me); 1.10 (1H,m,H-9); 1.20 (1H,m,H-16); 1.42 (1H,m,H-15); 1.51 (1H,m,H-7); 1.62 (1H,m,H-6); 1.69 & 2.26 (2H,m & m,H-20); 1.76 (1H,m,H-8); 1.86 (1H,m,H-14); 1.87 & 2.20 (2H,m & m,H-21); 3.34 (3H,m,—O—CH$_3$); 5.05 (1H,m,H-22); 6.02 (1H,m,H-4).

$^{13}$C NMR {125 MHz, CDCl$_3$(TMS), δ(ppm)}: 8.9 (CP(15β,16β)(CH$_2$)); 15.5 (C-15): 17.6 (C-19); 18.9 (CP(6β,7β)(CH$_2$)); 19.1 (C-6); 20.1 (C-7); 20.2 (C-18); 25.1 (C-16); 31.7 (C-20); 32.7 (C-21); 34.7 (C-8); 51.9 (C-9); 53.1 (C-14); 55.0 (—O—CH$_3$); 94.5 (C-17); 104.9 (C-22); 125.7 (C-4); 171.9 (C-5); 198.0 (C-3).

EXAMPLE 16

17-Hydroxy-6ξ,7ξ;15β,16β-bismethylene-3-oxo-17α-pregn-4-ene-21-carboxaldehyde cyclic 1,2-ethanediyl acetal 13.5 g of trimethylsulfoxonium-iodide is stirred in 250 ml of dry dimethyl sulfoxide under nitrogen for 5-10 minutes. To this suspension 3.5 g of potassium hydroxide is added and stirring is continued for 1 hour (potassium hydroxide is not fully dissolved). To the reagent prepared 5.0 g of (17α)-15β,16β-methylene-17-hydroxy-3-oxo-pregna-4,6-diene-21-carboxaldehyde cyclic 1,2-ethanediyl-acetal is added and stirring is continued under nitrogen atmosphere (the mixture becomes homogeneous after 2-4 hours).

Then the reaction is monitored by HPLC. After 20-24 hours the reaction mixture is slowly added to 2500 ml of water cooled to 10-12° C. and is stirred until the precipitate formed is dense enough to filter (about 2 hours). The crystals are filtered, washed to neutral with water, dried in vacuo to constant weight at a temperature below 40° C. 4.33 g (83.7%) crude title compound is obtained which is a mixture of 6β,7β- and 6α,7α-isomers of about 1:3 ratio.

NMR assignation of the 6β,7β-isomer in the mixture:
$^1$H NMR {500 MHz, CDCl$_3$(TMS), δ(ppm)}: 0.34 & 1.10 (2H,m & m,CP(15β16β)(CH$_2$)); 0.86 & 1.20 (2H,m & m,CP(6β,7β)(CH$_2$)); 0.93 (3H,s,18-Me); 1.10 (3H,d,19-Me); 1.10 (1H,m,H-9); 1.40 (1H,m,H-15); 1.40 (1H,m,H-16); 1.50 (1H,m,H-7); 1.61 (1H,m,H-6); 1.68 & 1.75 (2H,m & m,H-20); 1.76 (1H,m,H-8); 1.96 & 2.07 (2H,m & m,H-21); 1.97 (1H,m,H-14); 3.88 & 4.00 (4H,m & m,2×—O—CH$_2$—); 4.95 (1H,m,H-22); 6.02 (1,m,H-4).

$^{13}$C NMR {125 MHz, CDCl$_3$(TMS), δ(ppm)}: 7.9 (CP(15β,16β)(CH$_2$)); 16.1 (C-15); 17.6 (C-19); 18.9 (CP(6β,7β)(CH$_2$)); 19.0 (C-6); 19.2 (C-18); 20.2 (C-7); 23.04 (C-16); 28.34 (C-21); 30.88 (C-20); 34.8 (C-8); 52.1 (C-9); 52.6 (C-14); 64.98 & 65.01 (2×—O—CH$_2$—); 81.8 (C-17); 104.94 (C-22); 125.7 (C-4); 171.9 (C-S); 198.0 (C-3).

NMR assignation of the 6α,7α-isomer in the mixture:
$^1$H NMR {500 MHz, CDCl$_3$(TMS), δ(ppm)}: 0.30 & 1.06 (2H,m & m,CP(15β,16β)(CH$_2$)); 0.57 & 0.90 (2H,m & m,CP(6β,7β)(CH$_2$)); 0.80 (1H,m,H-9); 1.00 (3H,s,18-Me); 1.15 (3H,d,19-Me); 1.34 (1H,m,H-15); 1.35 (1H,m,H-16); 1.51 (1H,m,H-7); 1.68 & 1.75 (2H,m & m,H-20); 1.73 (1H,m,H-14); 1.79 (1H,m,H-6); 1.96 & 2.07 (2H,m & m,H-21); 2.23 (1H,m,H-8); 3.88 & 4.00 (4H,m & m,2×—O—CH$_2$—); 4.94 (1H,m,H-22); 5.95 (1H,m,H-4).

$^{13}$C NMR {125 MHz, CDCl$_3$(TMS), δ(ppm)}: 7.6 (CP(15β,16β)(CH$_2$)); 8.7 (CP(6α,7α)(CH$_2$)); 15.0 (C-7); 15.77 (C-6); 15.84 (C-15); 17.2 (C-19); 19.5 (C-18); 22.94 (C-16); 28.33 (C-21); 30.7 (C-8); 30.86 (C-20); 42.0 (C-9); 51.2 (C-14); 64.97 & 65.0 (2×—O—CH$_2$—); 82.0 (C-17); 105.00 (C-22); 126.6 (C-4); 172.4 (C-5); 198.06 (C-3).

EXAMPLE 17

6ξ,7ξ;15β,16β-Bismethylene-3-oxo-androst-4-ene-[17(β-1')spiro-5']-perhydrofuran-2'ξ-ol-methyl ether 4 g of the product obtained in Example 16 is dissolved in methanol, the solution is cooled to 0° C. and 10 ml of concentrated hydrochloric acid is added at 0° C. under continuous cooling. After stirring for 1 hour the precipitate formed is filtered, washed with portions of water until is free from acid, then dried in vacuo to constant weight at a temperature below 40° C. to yield 2.9 g (78.3%) of the crude title compound having 58% 6β,7β-isomer content.

EXAMPLE 18

6ξ,7ξ,15β,16β-Bismethylene-3-oxo-androst-4-ene-[17(β-1')spiro-5']-perhydrofuran-2'ξ-ol-propyl ether 10.2 g of Trimethylsulfoxonium iodide is stirred in 92 ml of dry dimethyl sulfoxide under nitrogen for 5-10 minutes. To this suspension 2.6 g of potassium hydroxide is added and stirring is continued for 1 hour (dissolution of the potassium hydroxide is not complete). To the reagent prepared 4.6 g of 15β,16β-methylene-3-oxo-androsta-4,6-diene-[17(β-1') spiro-5']-perhydrofuran-2'ξ-ol-propyl ether is added and stirring is continued under nitrogen atmosphere (the reaction mixture becomes homogeneous after 2-4 hours).

The reaction is monitored by HPLC. After 20-24 hours the reaction mixture is slowly added to 1000 ml of water cooled to 10-12° C. The precipitate formed is -stirred for 2 hours, and when dense enough the crystals are filtered, washed to neutral with water and dried in vacuo to constant weight at a temperature below 40° C. to yield 4.4 g (92.8%) of the crude title compound.

Since the propyl ether on the lactol ring may have α- or β-configuration and similarly the methylene ring in positions 6,7 may have α- or β-arrangement, four isomers were obtained which were separated by preparative HPLC.

NMR data of the pure 6β,7β;15β,16β-bismethylene-3-oxo-androst-4-ene-[17(β-1')spiro-5']-perhydrofuran-2'ξ-ol-propyl ether:

$^1$H NMR {500 MHz, CDCl$_3$(TMS), δ(ppm)}: 0.39 & 1.18 (2H,m & m,CP(15β,16β)(CH$_2$)); 0.86 & 1.20 (2H,m & m,CP (6β,7β)(CH$_2$)); 0.90 (3H,t,—O—CH$_2$—CH$_2$—CH$_3$); 0.95 (3H,s,18-Me); 1.10 (3H,d,19-Me); 1.10 (1H,m,H-9); 1.19 (1H,m,H-16); 1.41 (1H,m,H-15); 1.51 (1H,m,H-7); 1.56 (2H, m,—O—CH$_2$—CH$_2$—CH$_3$); 1.62 (1H,m,H-6); 1.69 & 2.27 (2H,m & m,H-20); 1.75 (1H,m,H-8); 1.86 (1H,m,H-14); 1.88 & 2.19 (2H,m & m,H-21); 3.33 & 3.64 (4H,m & m,—O—CH$_2$—CH$_2$—CH$_3$); 5.15 (1H,m,H-22); 6.02 (1H, m,H-4).

$^{13}$C NMR {125 MHz, CDCl$_3$(TMS), δ(ppm)}: 8.9 (CP (15β,16β)(CH$_2$)); 10.8 (—O—CH$_2$—CH$_2$—CH$_3$); 15.4 (C-15): 17.6 (C-19); 18.9 (CP(6β,7β)(CH$_2$)); 19.1 (C-6); 20.1 (C-7); 20.2 (C-18); 23.0 (—O—CH$_2$—CH$_2$—CH$_3$); 25.2 (C-16); 31.8 (C-20); 32.7 (C-21); 34.7 (C-8); 51.9 (C-9); 53.1 (C-14); 69.4 (—O—CH$_2$—CH$_2$—CH$_3$); 94.3 (C-17); 103.7 (C-22); 125.7 (C-4); 172.0 (C-5); 198.0 (C-3).

EXAMPLE 19

17-Hydroxy-3-oxo-6ξ,7ξ;15β,16β-bismethylene-17α-pregn-4-ene-21-carboxylic acid γ-lactone (Crude drospirenon)

8.00 kg of 6ξ,7ξ;15β,16β-bismethylene-3-oxo-androst-4-ene-[17(β-1')spiro-5']-perhydrofuran-2'ξ-ol-methyl ether is dissolved in 80 l of acetone, the solution is cooled to 0-2° C. and under vigorous stirring 24 l of Jones-reagent is added while the temperature is maintained at 0-5° C. Stirring is continued for 1 hour at 0-5° C. then the excess of the Jones-reagent is decomposed with 32 l of isopropanol at the same temperature. The mixture is stirred for 30 minutes, then 180 l water is added to the mixture in acetone containing a heterogenous portion, too. The acetone and the excess of the isopropanol are removed by distillation under reduced pressure. The aqueous suspension (the residue) is cooled to 25° C. and stirred until the precipitate is dense enough to filter (1 hour). The crystalline substance is filtered by centrifuge and washed to neutral with several portions of water and dried in vacuo to constant weight. The crude product (7.62 kg) in 80 l of ethyl acetate is clarified with 0.76 kg of activated carbon, then carbon is removed by filtration and the filtrate is evaporated to dryness to give 6.15 kg of oily product (drospirenon content is 60%) which is purified by chromatography.

EXAMPLE 20

17-Hydroxy-3-oxo-6ξ,7ξ;15β,16β-bismethylene-17α-pregn-4-ene-21-carboxylic acid γ-lactone (Crude drospirenon)

From 3.0 g of 6ξ,7ξ;15β,16β-Bismethylene-3-oxo-androst-4-ene-[17(β-1')spiro-5']-perhydrofuran-2'ξ-ol-propyl ether 2.75 g of crude title compound was prepared in a manner described in Example 19 and was purified as described in Example 19.

EXAMPLE 21

Pre-Purification of 17-Hydroxy-3-oxo-6ξ,7ξ,15β, 16β-bismethylene-17α-pregn-4-ene-21-carboxylic acid γ-lactone (drospirenone) by Low Pressure Chromatography Operating in Normal Phase Mode The column (diameter: 32 cm; length: 250 cm) was packed with 90 kg of silica gel (Merck Kieselgel, 40-60 μm particle size) by using the slurry method. 2.5 kg of crude drospirenone is dissolved in 13.5 l of dichloromethane and the solution in gravitation way is layered to the top of the silica gel bed, then is washed in with the eluent mixture (diisopropyl ether/ethyl acetate/dichloromethane of 57:33:10 v/v ratio) also in gravitation way. The column is filled up with the eluent, closed, and the elution is started with a flow rate of 200 l/hour. After 600 l of eluent had come down, fractions of 50 l are collected (about 20 fractions) and checked by TLC. Based on the TLC results fractions are formed: one that is "rich in 6α,7α isomer", another "mixed" fraction and one containing the "pre-purified drospirenone". Each fraction is evaporated to dryness, the solids obtained are crystallized from dichloromethane/diisopropyl ether (10:90 v/v %). The "mixed" fraction—besides the target compound (drospirenon)—contains the 6α,7α-isomer nearly in an amount as it present in the starting material. The "pre-purified drospirenone" contains maximum 2% 6α,7α-isomer. From 2.5 kg of crude drospirenone about 1.1 kg of "pre-purified" drospirenone is obtained, while the "mixed" fraction weighs about 0.6 kg. The latter one can be recirculated into the pre-chromatographic operation.

Total amount of the "pre-purified" product is 1353 g (54.6%).

Recovery of the 17-hydroxy-6α,7α;15β,16β-bismethylene-3-oxo-17α-pregn-4-ene-21-carboxylic acid γ-lactone (drospirenone, 6α,7α-isomer)

The evaporation residue obtained from the fraction "rich in 6α,7α-isomer" is crystallized first from acetone/diisopropyl ether (10:90 v/v %), then from methanol/water mixture and gave the pure drospirenone 6α,7α-isomer.

Mp: 202-203° C.

[α]$_D^{25}$=+134° (c=0.5%, chloroform).

UV: λ$_{max}$: 259 nm, ε=17811 (ethanol).

$^1$H NMR {500 MHz, CDCl$_3$(TMS), δ(ppm)}: 0.50 & 1.30 (2H,m & m,CP(15β,16β)(CH$_2$)); 0.57 & 0.94 (2H,m & m,CP (6α,7α)(CH$_2$)); 0.81 (1H,m,H-9); 1.06 (3H,s,18-Me); 1.16 (3H,d,19-Me); 1.32 (1H,m,H-16); 1.52 (1H,m,H-7); 1.53 (1H,m,H-15); 1.72 (1H,m,H-14); 1.82 (1H,m,H-6); 2.10 & 2.42 (2H,m & m,H-20); 2.25 (1H,m,H-8); 2.51 & 2.62 (2H, m & m,H-21); 5.96 (1H,m,H-4).

$^{13}$C NMR {125 MHz, CDCl$_3$(TMS), δ(ppm)}: 8.6 (CP(6α, 7α)(CH$_2$)); 9.7 (CP(15β,16β)(CH$_2$)); 14.6 (C-7): 15.7 (C-6); 16.4 (C-15); 17.1 (C-19); 20.05 (C-18); 24.3 (C-16); 29.3 (C-21); 30.3 (C-8); 30.7 (C-20); 41.9 (C-9); 50.6 (C-14); 96.3 (C-17); 126.8 (C-4); 171.6 (C-5); 176.6 (C-22); 197.9 (C-3).

Fine Chromatography by HPLC

The column (diameter: 20 cm) is packed with 8 kg of silica gel (UETIKON C-GEL C-490; particle size: 15-35 μm) by the slurry method (compacted length of the adsorbent: about 60 cm) and conditioned with the eluent used for pre-chromatography. 80 g of pre-purified drospirenone (max. 6α,7α-isomer content is 2%) is dissolved in 600 ml of dichloromethane and the solution is injected to the column. Elution is carried out with a flow rate of 80 l/hour and the eluent leaving then column is subjected to UV detection. From the breakthrough of the compound a pre-fraction (3.6 l) is collected containing an isomeric mixture; then the "fine chromatographed" fraction is collected upon UV detection (about 20 l). Both fractions are evaporated and the residues are crystallized from dichloromethane/diisopropyl ether (10:90 v/v %). The pre-fraction yielded 20-25 g of crystalline substance (max. 2% 6α,7α-isomer content), the "fine chromatographed" fraction gave 55-60 g of drospirenone (max. 0.1% 6α,7α-isomer content). The pre-fraction was recirculated into the fine chromatography; such way the total amount of drospirenone is 75 g (93.7%).

From 2.5 kg crude product 1268 g (50.73%) crystalline product was obtained, which was dissolved in 12.5 l isopropanol under reflux, then cooled to 0° C., the crystalline substance was filtered, the mother liquor was washed away with 500 ml of isopropanol, then dried to constant weight giving 1230 g (49.2%) of crystalline product.

Crystallization can also be carried out with the same result from the solvents follows: methanol, ethanol, propanol, isopropanol, ethyl acetate, a solvent mixture containing water up to 10 vol % selected from methanol/water, ethanol/water, propanol/water; isopropanol/water; acetone/diisopropyl ether mixture containing acetone up to 50 vol %; cyclohexane/ethyl acetate mixture containing, ethyl acetate up to 50 vol %; dichloromethane/diisopropyl ether mixture containing dichloromethane up to 10 vol %; and dichloromethane/hexane mixture containing dichloromethane up to 10 vol %.

Mp: 201° C.

$[\alpha]_D^{25} = -182°$ (c=1, dichloromethane).

$^1$H NMR {500 MHz, CDCl$_3$(TMS), δ(ppm)}: 0.53 & 1.33 (2H,m & m,CP(15β,16β)(CH$_2$)); 0.87 & 1.22 (2H,m & m,CP(6β,7β)(CH$_2$)); 1.00 (3H,s,18-Me); 1.10 (3H,d,19-Me); 1.12 (1H,m,H-9); 1.36 (1H,m,H-16); 1.50 (1H,m,H-7); 1.59 (1H,m,H-15); 1.64 (1H,m,H-6); 1.79 (1H,m,H-8); 1.95 (1H,m,H-14); 2.11 & 2.44 (2H,m & m,H-20); 2.53 & 2.64 (2H,m & m,H-21); 6.03 (1H,m,H-4).

$^{13}$C NMR {125 MHz, CDCl$_3$(TMS), δ(ppm)}: 10.0 (CP(15β,16β)(CH$_2$)); 16.6 (C-15); 17.6 (C-19); 18.8 (CP(6β,7β)(CH$_2$)); 19.0 (C-6); 19.73 (C-18); 19.75 (C-7); 24.6 (C-16); 29.3 (C-21); 30.7 (C-20); 34.3 (C-8); 51.7 (C-9); 51.9 (C-14); 96.1 (C-17); 125.9 (C-4); 171.1 (C-5); 176.5 (C-22); 197.8 (C-3).

Chromatography can also be accomplished with the mixtures follows: cyclohexane/ethyl acetate/acetone mixture of the 64:18:18 v/v ratio, cyclohexane/ethyl acetate/acetonitrile of the 55:35:10 v/v ratio or cyclohexane/methyl tert-butyl ether/acetone mixture of the 50:30:20 v/v ratio, while the adsorbent given above is used.

EXAMPLE 22

17-Hydroxy-3-oxo-6β,7β;15β,16β-bismethylene-17α-pregn-4-ene-21-carboxylic acid γ-lactone 8.00g of 6β,7β;15β,16β-bismethylene-3-oxoandrost-4-ene[17(β-1')spiro-5']-perhydrofuran-2'ξ-ol methyl ether is dissolved in 80 ml of acetone. The solution is cooled to 0-2° C. and under vigorous stirring 24 ml of Jones-reagent is added while the temperature is maintained at 0-5° C. The mixture is stirred for 1 hour at 0-5° C., then the excess of the Jones-reagent is decomposed with 32 ml of isopropanol while temperature is kept at the same level. After stirring for 30 minutes 100 ml of water is added to the acetone solution containing some heterogeneous part too, then the acetone and the excess of isopropanol is distilled off under reduced pressure. The residue (an aqueous suspension) is cooled to 25° C., stirred for 1 hour until the precipitate becomes dense and then filtered by centrifuge. The crystals obtained are washed to neutral with portions of water and dried in vacuo to constant weight. The crude product (7.7 g) in 80 ml of ethyl acetate is clarified with activated carbon (0.77 g), filtered and the filtrate is evaporated to dryness. The crystalline residue is recrystallized from isopropanol to give 6.28 g (82%) of the title compound.

Mp: 201-202° C.

EXAMPLE 23

17-Hydroxy-3-oxo-6β,7β,15β,16β-bismethylene-17α-pregn-4ene-21-carboxylic acid γ-lactone From 4 g of 6β,7β;15β,16β-bismethylene-3-oxoandrost-4-ene[17(β-1')spiro-5']-perhydrofuran-2'ξ-ol-propyl ether and following the method described in example 20, 2.71 g (76.6%) of the title compound is obtained.

The invention claimed is:

1. Industrial process for the preparation of 17-hydroxy-6β, 7β; 15β,16β-bismethylene-3-oxo-17α-pregn-4-ene-21-carboxylic acid γ-lactone of the formula (I)

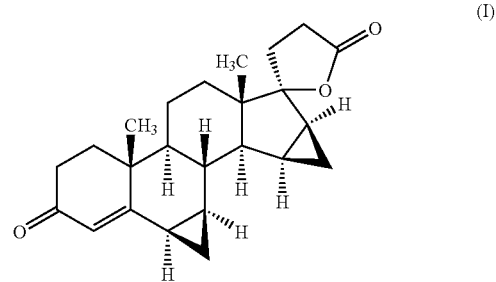

from the known 15α-hydroxy-androst-4-ene-3,17-dione of the formula (III) characterized in that the 15α-hydroxy-androst-4-ene-dione of the formula (III)

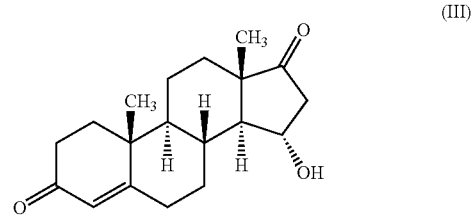

is esterified on the hydroxy in position 15 with a reactive derivate of a $C_{1-6}$ alkane carboxylic acid in the presence of a catalytic amount of 4-dimethyl-aminopyridine to yield a 15α-acyloxyandrost-4-ene-3,17-dione of the general formula (IV),

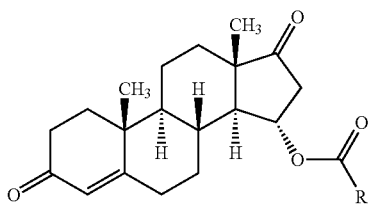
(IV)

wherein R stands for hydrogen atom or an alkyl group having 1-5 carbon atoms, said compound of the general formula (IV) is reacted in the presence of an acidic catalyst with a trialkyl orthoformiate having 1-4 carbon atoms in the alkyl moieties to give 15α-acyloxy-3-alkoxy-androsta-3,5-diene-17-one of the general formla (V),

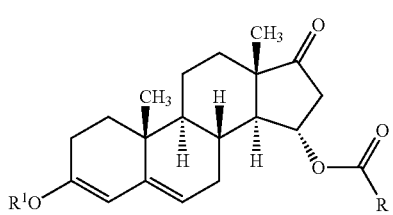
(V)

wherein R has the same meaning as defined above and $R^1$ stands for an alkyl group having 1-4carbon atoms, said compound of the general formula (V) is reacted with trimethylsulfoxonium methylide prepared in situ in dimethyl sulfoxide from a trimethylsulfoxonium salt and an alkali metal hydroxide to yield 15β,16β-methylene-3-alkoxyandrosta-3,5-diene-17-one of the general formula (VI),

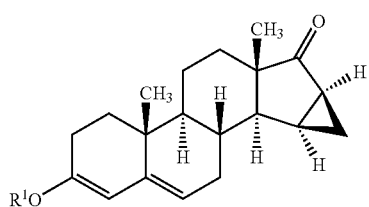
(VI)

wherein $R^1$ has the same meaning as defined above, said compound of the general formula (VI) is reacted in the presence of lithium metal with 2-(2-bromoethyl)-1,3-dioxolane or 2-(2-bromoethyl)-dialkoxy-acetal having 1-4carbon atoms in the alkoxy moieties, to give 17-hydroxy-15β,16β-methylene-3-alkoxy-17α-pregna-3,5-diene-21-carboxaldehyde-cyclic 1,2-ethanediyl acetal or the 17-hydroxy-15β,16β-methylene-3-alkoxy-17α-pregna-3,5-diene-21-carboxaldehyde dialkoxyacetal of general formula (VII)

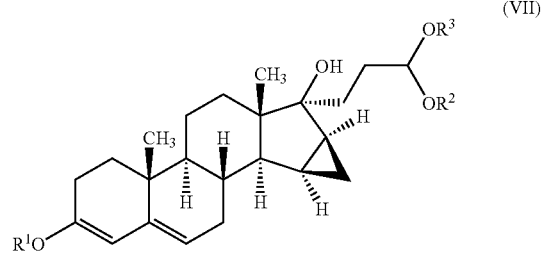
(VII)

wherein $R^1$ has the same meaning as defined above and $R^2$ and $R^3$ stand for an alkyl group having 1-4carbon atoms or form together a 1,2-ethylene group, said compound of the general formula (VII) is oxidized with chloranil (2,3,5,6-tetrachloro-2,5-cyclohexadiene-1,4-dione) to form 17-hydroxy-15β,16β-methylene-3-oxo-17α-pregna-4,6-diene-21-carboxaldehyde cyclic 1,2-ethanediyl-acetal or 17α-hydroxy-15β,16β-methylene-3-oxo-17α-pregna-4,6-diene-21-carboxaldehyde dialkoxy-acetal of the general formula (VIII)

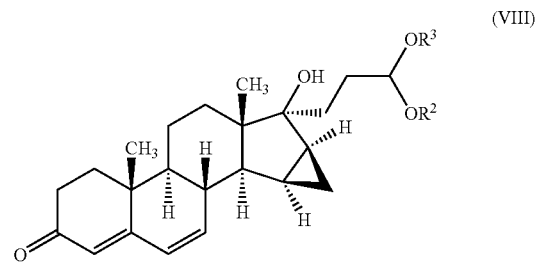
(VIII)

wherein $R^2$ and $R^3$ have the same meaning as defined above, said compound of the general formula (VIII)

a) is cyclized in acidic medium to form 15β,16β-methylene-3-oxo-androsta-4,6-diene-[17(β-1)spiro5']-perhydrofuran-2'ξ-ol-alkyl ether of the general formula (IX)

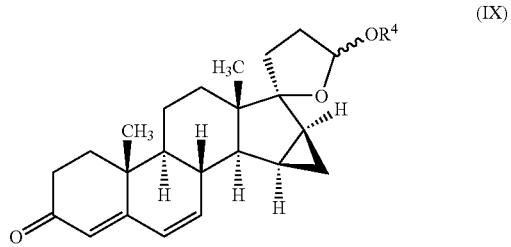
(IX)

wherein R⁴ stands for methyl, ethyl or propyl group and the ~ bond represents α and β configuration, and said compound of the formula (IX) is reacted with trimethylsulfoxonium methylide prepared in situ in dimethyl sulfoxide from a trimethylsulfoxonium salt and alkali metal hydroxide, or b) is reacted with trimethylsulfoxonium methylide prepared in situ in dimethyl sulfoxide from a trimethylsulfoxonium salt and alkali metal hydroxide; to give a bismethylene derivative of the general formula (IXa)

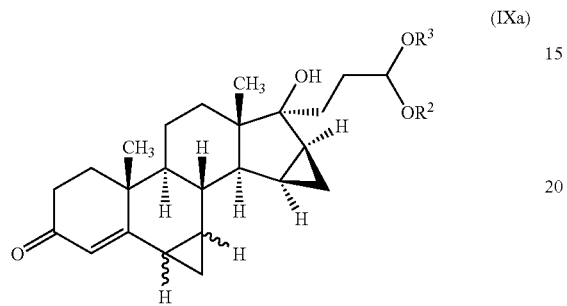

(IXa)

wherein R² and R³ have the same meaning as defined above and the ~ bond represents α and β configuration, and said compound of the general formula (IXa) is cyclized in acidic medium, then from the 6ξ,7ξ;15β,16β-bismethylene-3-oxo-androst-4-ene-[17(β-1)spiro5']-perhydrofuran-2'ξ-ol-alkyl ether mixture of the general formula (X) obtained at the end in any of the above alternative step sequences

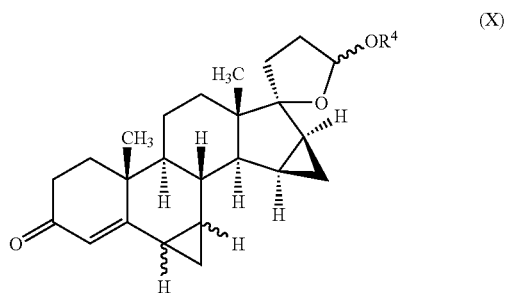

(X)

wherein R⁴ stands for methyl, ethyl or propyl group and the ~ bond represents α and β configuration, the 6β;7β-isomer is separated by chromatography and oxidized with the Jones-reagent to give the drospirenone, or the 6ξ,7ξ;15β,16β-bismethylene-3-oxo-androst-4-ene-[17(β-1)spiro5']-perhydrofuran-2'ξ-ol-alkyl ether mixture of the general formula (X) obtained at the end in any of the above alternative step sequences, wherein R⁴ stands, for methyl, ethyl or propyl group and the ~ bond represents α and β configuration, is oxidized with Jones reagent to give 6ξ,7ξ; 15β,16β-bismethylene-3-oxo-androst-4-ene-[17(β-1)spiro5']-perhydrofuran-2 '-one (17-hydroxy-6ξ,7ξ; 15β,16β-bismethylene-3-oxo-17α-pregn-4-ene-21-carboxylic acid γ-lactone) of the general formula (XI)

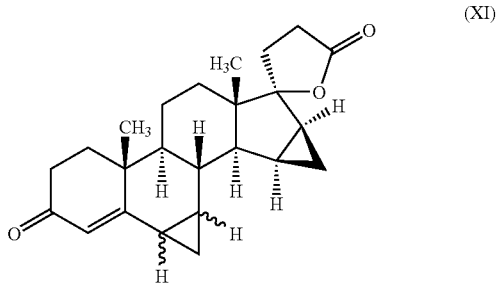

(XI)

wherein the ~ bond represents α and β configuration, and from this isomeric mixture the 6β,7β-isomer is isolated and if desired the drospirenone of the formula (I) obtained by any of the above synthesis routes is purified by crystallization.

2. A process according to claim 1, characterized in that the separation by chromatography of the isomeric products of the general formula (XI)—wherein the ~ bond represents α- and β- configuration—is carried out on silica gel adsorbent.

3. A process according to claim 1, characterized in that the separation by chromatography of the isomeric products of the general formula (XI)—wherein the ~ bond represents α- and β- configuration—is carried out in two steps, i.e. in a prechromatographic and in a fine chromatographic step.

4. A process according to claim 1, characterized in that the separation by chromatography of the isomeric products of the general formula (XI)—wherein the ~ bond represents α- and β- configuration—is carried out by using cyclohexane/ethyl acetate/acetone mixture of the 64:18:18 v/v ratio or cyclohexane/ethyl acetate/acetonitrile mixture of the 55:35:10 v/v ratio or cyclohexane/methyl tert-butyl ether/acetone mixture of the 50:30:20 v/v ratio or cyclohexane/acetone mixture of the 73:27 v/v ratio or diisopropylether/ethyl acetate/dichloromethane mixture of the 57:33:10 v/v ratio as eluent.

5. A process according to claim 1, characterized in that drospirenone of the formula (I) is crystallized from methanol, ethanol, propanol, isopropanol, ethyl acetate, or from a solvent mixture containing water up to 10 vol % selected from methanol/water, ethanol/water, propanol/water, isopropanol/water, acetone/diisopropyl ether mixture containing acetone up to 50 vol % cyclohexane/ethyl acetate mixture containing ethyl acetate up to 50 vol dichloromethane/diisopropyl ether mixture containing dichloromethane up to 10 vol % and dichloromethane/hexane mixture containing dichloromethane up to 10 vol %.

6. A process according to claim 1, wherein the esterification of the compound of formula (III) to yield the compound of the formula (IV) is carried out at not more than 40° C. in tetrahydrofuran.

7. The process according to claim 1 wherein the compound of formula (IV) is reacted in the presence of a catalytic amount of $H_2SO_4$ with a trialkyl orthoformiate to give the compound of the formula (V).

8. A process according to claim 1, wherein R¹ is methyl and the compound of formula (VI) is reacted with 2-(2-bromoethyl)-1,3-dioxolane and a resulting precipitate is crystallized from methanol to give the compound of the general formula (VII).

9. A process according to claim 1 wherein R stands for a hydrogen atom or an unbranched alkyl group having 1-4 carbon atoms.

10. A process according to claim 1 wherein $R^2$ and $R^3$ form together a 1,2-ethylene group.

11. A process according to claim 1 wherein the compound of the formula (VIII) or the compound of the formula (IXa) is cyclized in a strong acidic medium.

12. A process according to claim 1, wherein the compound of the formula (V) is crystallized from acetonitrile.

13. A process according to claim 1, the compound of the general formula (VI) is crystallized from methanol.

14. 6ξ,7ξ;15β,16β-Bismethylene-3-oxo-androst-4-ene-[17(β-1)spiro5']-perhydrofuran-2'ξ-ol-alkyl ethers of the general formula (X)

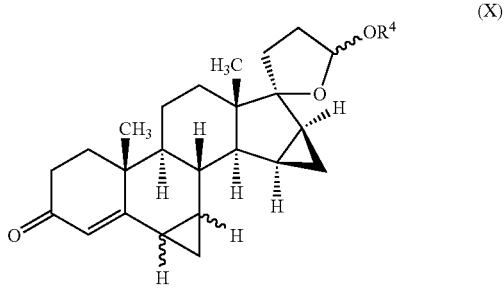

wherein $R^4$ stands for a methyl group and the ~ bond represents α- and β-configuration.

* * * * *

UNITED STATES PATENT AND TRADEMARK OFFICE
CERTIFICATE OF CORRECTION

PATENT NO. : 8,309,712 B2
APPLICATION NO. : 11/719333
DATED : November 13, 2012
INVENTOR(S) : Sörös et al.

It is certified that error appears in the above-identified patent and that said Letters Patent is hereby corrected as shown below:

In the title and column 1, "Y-LACTONE" should read -- γ-LACTONE --.
At column 24, line 33, "y-lactone" should read -- γ-lactone --.
At column 25, lines 35 and 62, and column 26, line 17, each occurrence, "1-4carbon" should read -- 1-4 carbon --.
At column 27, lines 64-65, "6ξ,7ξ; 15β,16β-bismethylene-3-oxo-androst-4-ene-[17(β-l)spiro5']-perhydrofuran-2 '-one" should read -- 6ξ,7ξ; 15β,16β-bismethylene-3-oxo-androst-4-ene-[17(β-1)spiro5']-perhydrofuran-2'-one --.
At column 28, line 50, "50 vol" should read -- 50 vol % --.

Signed and Sealed this
Twenty-sixth Day of February, 2013

Teresa Stanek Rea
*Acting Director of the United States Patent and Trademark Office*